(12) United States Patent
Chan et al.

(10) Patent No.: US 9,717,797 B2
(45) Date of Patent: Aug. 1, 2017

(54) POLYCARBONATES BEARING AROMATIC N-HETEROCYCLES FOR DRUG DELIVERY

(71) Applicants: International Business Machines Corporation, Armonk, NY (US); Agency For Science, Technology and Research, Singapore (SG); Universidad del Pais Vasco/Euskal Herriko Unibertsitatea, Bizkaia (ES)

(72) Inventors: Julian M. W. Chan, Fremont, CA (US); Amanda C. Engler, San Jose, CA (US); James L. Hedrick, Pleasanton, CA (US); Xiyu Ke, Singapore (SG); Victor W. L. Ng, Singapore (SG); Haritz Sardon, San Jose, CA (US); Jeremy P. K. Tan, Singapore (SG); Yi Yan Yang, Singapore (SG)

(73) Assignees: International Business Machines Corporation, Armonk, NY (US); Agency For Science, Technology And Research, Singapore (SG); Universidad del París Vasco/Euskal Herriko Unibertsitatea, Bizkaia (ES)

( * ) Notice: Subject to any disclaimer, the term of this patent is extended or adjusted under 35 U.S.C. 154(b) by 909 days.

(21) Appl. No.: 14/097,488

(22) Filed: Dec. 5, 2013

(65) Prior Publication Data

US 2015/0157723 A1 Jun. 11, 2015

(51) Int. Cl.
*A61K 9/00* (2006.01)
*A61K 47/34* (2017.01)
(Continued)

(52) U.S. Cl.
CPC ............ *A61K 47/34* (2013.01); *A61K 9/5146* (2013.01); *A61K 31/704* (2013.01);
(Continued)

(58) Field of Classification Search
CPC ...................................................... A61K 47/34
See application file for complete search history.

(56) References Cited

U.S. PATENT DOCUMENTS 6,329,379 B1   12/2001   Llinas-Brunet et al.
7,053,088 B2   5/2006   Doherty et al.
(Continued)

FOREIGN PATENT DOCUMENTS

CN     1384129 A     12/2002
EP     0458037 A1    11/1991
(Continued)

OTHER PUBLICATIONS

Attia, et al., "The effect of kinetic stability on biodistribution and anti-tumor efficacy of drug-loaded biodegradable polymeric micelles", Biomaterials, vol. 34, Issue 12, Apr. 2013, pp. 3132-3140.

(Continued)

*Primary Examiner* — Paul Dickinson
(74) *Attorney, Agent, or Firm* — Michael R. Roberts

(57) ABSTRACT

Nanoparticles comprise a drug, a first block polymer and a second block polymer. The first block polymer has a poly (ethylene oxide) (PEO) block and a polycarbonate block bearing a side chain aromatic nitrogen-containing heterocycle (N-heterocycle). The N-heterocycle can be in the form of a base, a hydrosalt of the base, a sulfobetaine adduct of the base, or a combination thereof. The second block polymer has a PEO block and a polycarbonate block bearing a side chain catechol group, which can be present as a catechol, oxidized form of a catechol, and/or a polymerized (Continued)

form of a catechol. The nanoparticles can be dispersed in water and are capable of controlled release of the drug.

18 Claims, 5 Drawing Sheets

(51) Int. Cl.
    *A61K 31/704*     (2006.01)
    *A61K 31/713*     (2006.01)
    *A61K 9/51*     (2006.01)
    *C08G 64/02*     (2006.01)
    *C08G 64/18*     (2006.01)
    *A61K 38/16*     (2006.01)
    *A61K 38/00*     (2006.01)

(52) U.S. Cl.
    CPC ........ *A61K 31/713* (2013.01); *C08G 64/0241* (2013.01); *C08G 64/183* (2013.01); *A61K 38/00* (2013.01); *A61K 38/16* (2013.01)

(56) References Cited

U.S. PATENT DOCUMENTS

| | | |
|---|---|---|
| 7,250,511 B2 | 7/2007 | Bavetsias |
| 2008/0166382 A1 | 7/2008 | Hsieh et al. |
| 2011/0319570 A1 | 12/2011 | Emrick |

FOREIGN PATENT DOCUMENTS

| | | | | |
|---|---|---|---|---|
| JP | 2007293222 A1 | 11/2007 | | |
| JP | 2008088194 A | 4/2008 | | |
| JP | 2009040709 A | 2/2009 | | |
| KR | 1020140133738 B1 | 11/2014 | | |
| WO | 2010146029 A2 | 12/2010 | | |
| WO | 2010146032 A2 | 12/2010 | | |
| WO | 2011078803 A1 | 6/2011 | | |
| WO | WO 2011078803 A1 * | 6/2011 | ........... | A61K 9/1075 |
| WO | 2011135046 A1 | 11/2011 | | |

OTHER PUBLICATIONS

Mindemark, et al., "Diversity in cyclic carbonates: synthesis of triazole-functional monomers using click chemistry", Polym. Chem., 2012,3, 1399-1401.
JPO, PCT International Search Report, PCT/JP2014006043, Jan. 20, 2015.
JPO, PCT Transmitall of ISR-WO, PCT/JP2014006043, Jan. 20, 2015.
JPO, PCT Written Opinion, PCT/JP2014006043, Jan. 20, 2015.
Sanders et al., "A Simple and Efficient Synthesis of Functionalized Cyclic Carbonate Monomers Using a Versatile Pentafluorophenyl Ester Intermediate", J. Am. Chem. Soc., 2010, 132 (42), pp. 14724-14726.
Edward, et al., "Organocatalytic Synthesis of Quinine-Functionalized Poly(carbonate)s," Biomacromolecules 2012, 13, 2483-2489; published Jul. 31, 2012.
Engler, et al., "Accessing New Materials through Polymerization and Modification of a Polycarbonate with a Pendant Activated Ester," Macromolecules 2013, 46, 1283-1290; Published: Feb. 7, 2013.
S. Tempelaar, "Synthesis and post-Polymerisation Functionalisation of Aliphatic Poly(carbonate)s," Thesis, University of Warwick, Mar. 2012.
Yang, et al., "The role of non-covalent interactions in anticancer drug loading and kinetic stability of polymeric micelles," Biomaterials 33 (2012) 2971-2979; Available online Jan. 13, 2012.
Yang, et al., "Supramolecular nanostructures designed for high cargo loading capacity and kinetic stability," Nano Today (2010) 5, 515-523, plus Supplement.
Zhang, et al., "Cationic Polycarbonates Prepared Via Michael Addition of Amines on the Pendant Methacrylamido Groups," Acta Polymerica Sinica 2011 0 8 889-894, Abstract.
Zhang, et al., "A Water-Soluble Polycarbonate With Dimethylamino Pendant Groups Prepared by Enzyme-Catalyzed Ring-Opening Polymerization," Macromol. Rapid Commun. 2012, 33, 693-697; Published online: Feb. 21, 2012.

* cited by examiner

POLYCARBONATES BEARING AROMATIC N-HETEROCYCLES FOR DRUG DELIVERY

BACKGROUND

The present invention relates to polycarbonates bearing aromatic N-heterocycles for drug delivery, and more specifically to water dispersible nanoparticles formed with aromatic N-heterocycle-functionalized polycarbonates and catechol-functionalized polycarbonates for delivering drugs used in medical treatments.

Drug delivery systems that rely on polymers as vehicles for carrying a drug have several deficiencies, particularly those involving hydrophobic drugs (e.g., Doxorubicin, an anthracycline antibiotic used in chemotherapy, known for its hydrophobicity, toxicity, and difficulty in packaging in a water based delivery system). Generally, the polymers are non-biodegradable. Another deficiency is the susceptibility of nanoparticles to serum protein induced aggregation, which causes undesirable particle size growth in the blood stream. Another deficiency is the propensity of drug carriers to leak drug in the blood stream, which can lower the efficacy of the drug with respect to its intended target and expose patients to toxic side effects of the released drug that the drug-loaded particle was intended to mitigate. Another deficiency is the cytotoxicity of the polymer vehicle itself.

As a result, a need exists for a biodegradable, non-cytotoxic drug delivery system that is not susceptible to protein induced aggregation (i.e., is "anti-fouling" in the blood stream), and does not prematurely release drug before reaching an intended cell target.

SUMMARY

Accordingly, a nanoparticle is disclosed, comprising:
a drug;
a first block polymer comprising i) a first poly(ethylene oxide) block (first PEO block) and ii) a first polycarbonate block linked to the first PEO block, wherein a) the first polycarbonate block comprises a first repeat unit comprising an aliphatic carbonate backbone portion and a side chain linked to the backbone portion, b) the side chain of the first repeat unit comprises an aromatic nitrogen-containing heterocycle (N-heterocycle), and c) the N-heterocycle of the side chain of the first repeat unit is present as a base, a hydrosalt of the base, a sulfobetaine adduct of the base, or a combination thereof; and
a second block polymer comprising i) a second PEO block and ii) a second polycarbonate block linked to the second PEO block, wherein a) the second polycarbonate block comprises a second repeat unit comprising an aliphatic carbonate backbone portion and a side chain linked to the backbone portion and b) the side chain of the second repeat unit comprises a catechol group;
wherein
the drug, the first block polymer, and the second block polymer of the nanoparticle are bound at least by non-covalent interactions,
the nanoparticle is water-dispersible, and
the nanoparticle is capable of controlled release of the drug in a medical treatment.

Also disclosed is a method, comprising:
forming a first mixture comprising a drug and a water miscible organic solvent; forming a second mixture by dissolving together in water a first block polymer and a second block polymer;
combining the first mixture and the second mixture, thereby forming a third mixture; and
removing the organic solvent from the third mixture, thereby forming a water dispersible nanoparticle comprising the drug, the first block polymer, and the second block polymer bound at least by non-covalent interactions;
wherein
the first block polymer comprises i) a first poly(ethylene oxide) block (first PEO block) and ii) a first polycarbonate block linked to the first PEO block, wherein the first polycarbonate block comprises a first repeat unit, the first repeat unit comprises an aliphatic carbonate backbone portion and a side chain linked to the backbone portion, the side chain of the first repeat unit comprises an aromatic nitrogen-containing heterocycle (N-heterocycle), and the N-heterocycle has the form of a base, a hydrosalt of the base, a sulfobetaine adduct of the base, or a combination thereof,
the second block polymer comprises i) a second PEO block and ii) a second polycarbonate block linked to the second PEO block, wherein the second polycarbonate block comprises a second repeat unit comprising an aliphatic carbonate backbone portion and a side chain linked to the backbone portion, and the side chain of the second repeat unit comprises a catechol group, and
the nanoparticle is capable of controlled release of the drug in a medical treatment.

Also disclosed is a nanoparticle, comprising:
a) a drug;
b) a first block polymer having the formula (1):

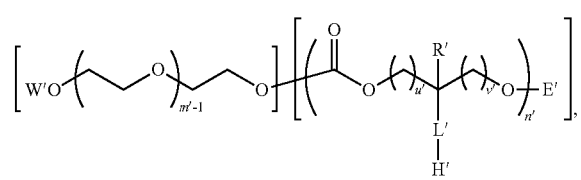

wherein
u' is a positive integer from 0 to 6,
v' is a positive integer from 0 to 6,
u' and v' cannot both be zero,
n' is a positive number of 2 to about 50,
m' is a positive number of about 80 to about 200,
E' is a monovalent end group selected from the group consisting of hydrogen and functional groups comprising 1 or more carbons,
H' is a functional group selected from the group consisting of non-charged aromatic nitrogen-containing heterocycles, hydrosalts of aromatic nitrogen-containing heterocycles, sulfobetaine adducts of aromatic nitrogen-containing heterocycles, and combinations thereof,
L' is a divalent linking group comprising 2 or more carbons,
R' is a monovalent radical selected from the group consisting of hydrogen and alkyl groups comprising 1 to 6 carbons, and
W' is a monovalent end group comprising 1 to 10 carbons; and c) a second block polymer having the formula (4):

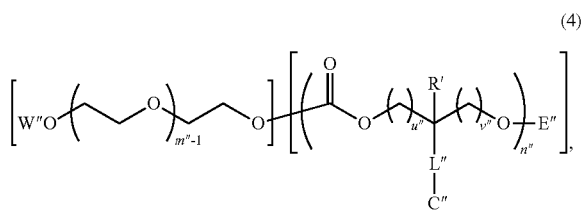

(4)

wherein
u" is a positive integer from 0 to 6,
v" is a positive integer from 0 to 6,
u" and v" cannot both be zero,
n" is a positive number of 2 to about 50,
m" is a positive number of about 80 to about 200,
E" is a monovalent end group selected from the group consisting of hydrogen and functional groups comprising 1 or more carbons,
C" is a moiety comprising a catechol group,
L" is a divalent linking group comprising 2 or more carbons,
R" is a monovalent radical selected from the group consisting of hydrogen and alkyl groups comprising 1 to 6 carbons, and
W" is a monovalent end group comprising 1 to 10 carbons;
wherein
components a), b), and c) of the nanoparticle are bound at least by non-covalent interactions,
the nanoparticle is dispersible in water, and
the nanoparticle is capable of controlled release of the drug in a medical treatment.

Also disclosed is a polycarbonate, comprising:
a first repeat unit comprising an aliphatic carbonate backbone portion and a side chain linked to the backbone portion, the side chain comprising an aromatic nitrogen-containing heterocycle (N-heterocycle), wherein the N-heterocycle is present in the first repeat unit as a free base (non-charged form), a hydrosalt of the free base, a sulfobetaine adduct of the free base, or a combination thereof.

The above-described and other features and advantages of the present invention will be appreciated and understood by those skilled in the art from the following detailed description, drawings, and appended claims.

DETAILED DESCRIPTION

Figure 1:
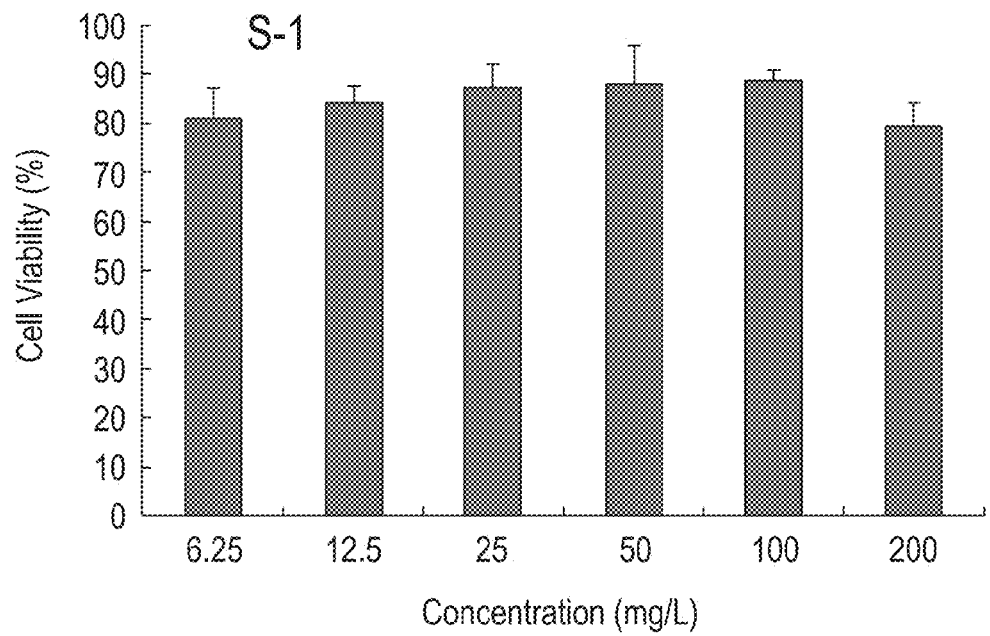
FIG. 1 is bar chart showing the toxicity profile of sulfobetaine polymer S-1 to HEK293 cells. S-1 is not cytotoxic.
Figure 2:
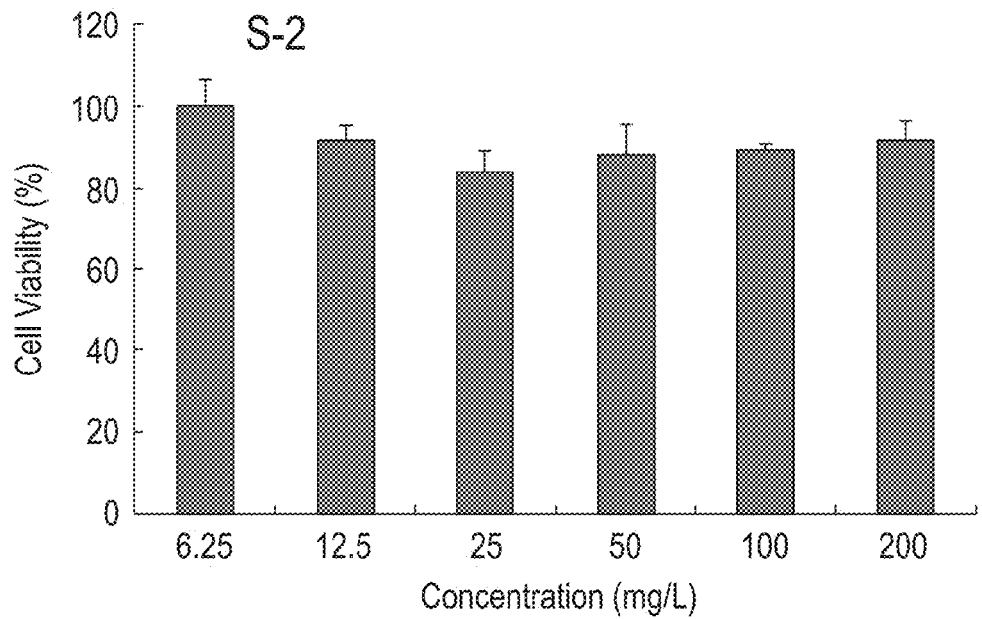
FIG. 2 is bar chart showing the toxicity profile of sulfobetaine polymer S-2 to HEK293 cells. S-2 is not cytotoxic.
Figure 3:
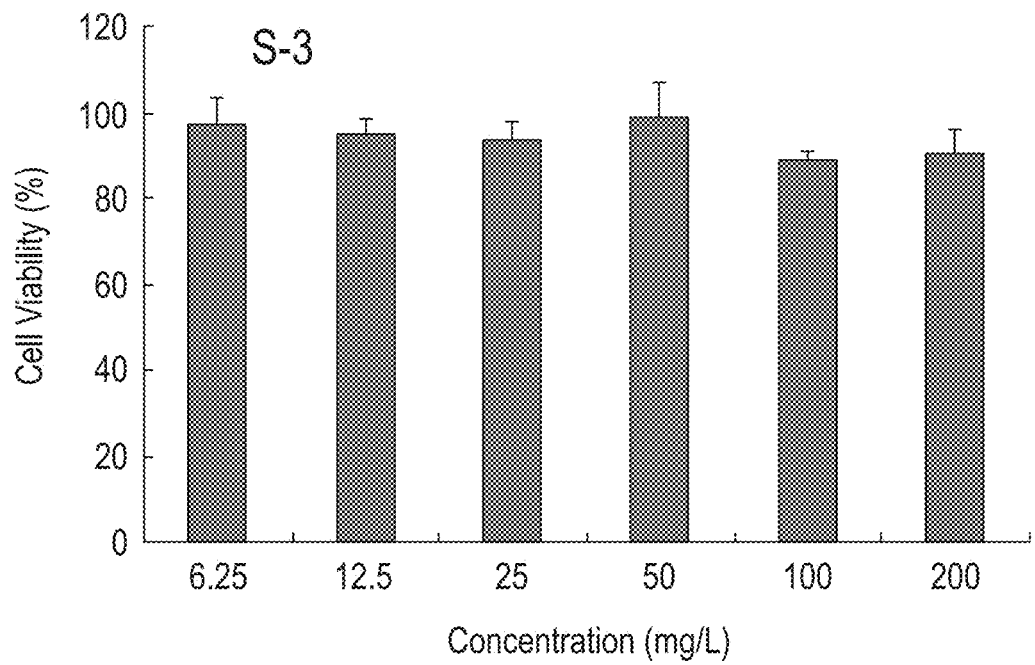
FIG. 3 is bar chart showing the toxicity profile of sulfobetaine polymer S-3 to HEK293 cells. S-3 is not cytotoxic.
Figure 4:
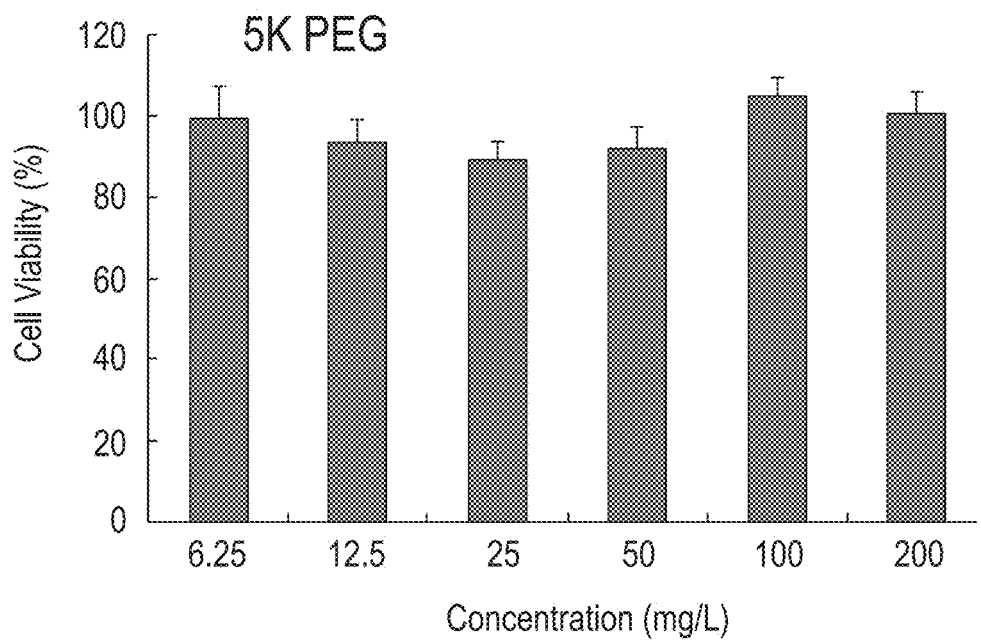
FIG. 4 is bar chart showing the toxicity profile of poly(ethylene glycol), Mn 5000, (5K PEG) to HEK293 cells. The 5K PEG is not cytotoxic.
Figure 5:
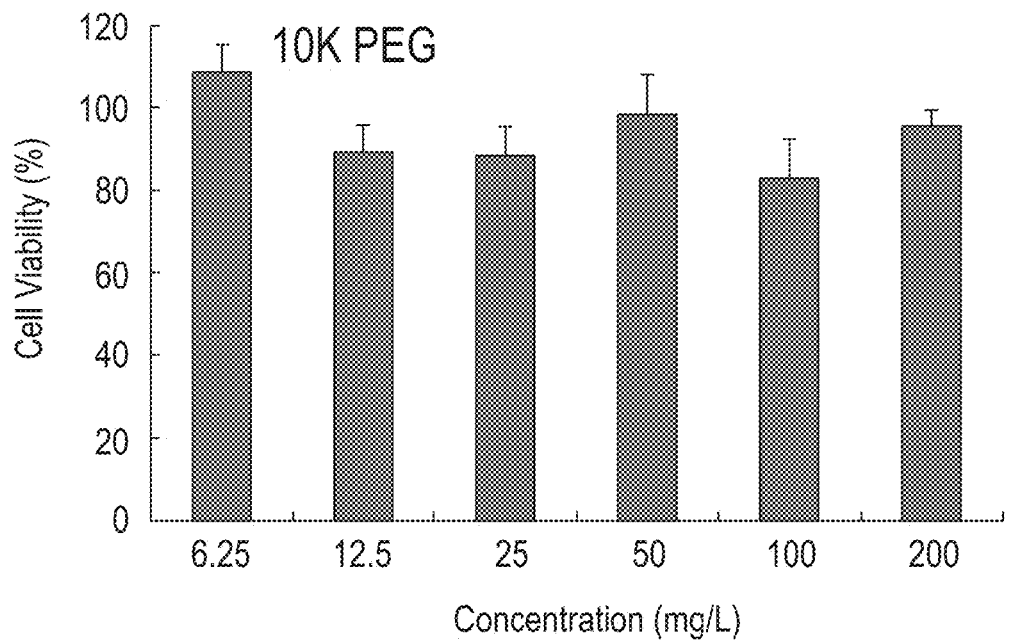
FIG. 5 is bar chart showing the toxicity profile of poly(ethylene glycol), Mn 10000, (10K PEG) to HEK293 cells. The 10K PEG is not cytotoxic.

Disclosed are water-dispersible nanoparticulate compositions comprising i) a drug, ii) a first block polymer comprising a pendant N-heterocycle, and iii) a second block polymer comprising a pendant catechol group. Unless otherwise stated, the use of the term "nanoparticle" herein means a particle containing the foregoing three components. The nanoparticle has an average diameter between 0 nanometers and 1 micrometer when dispersed in water. The foregoing three components of the nanoparticle are in contact with one another and bound at least by non-covalent interactions (e.g., hydrophobic bonding, hydrogen bonding). Due to the propensity of the catechol group to oxidize and or polymerize, the three components of the nanoparticle can also potentially be bound by non-covalent interactions. The nanoparticles are capable of controlled release of the drug in a medical treatment. The nanoparticles can be anti-fouling (i.e., less prone to aggregate when contacted by serum protein) and/or transparent to macrophages, giving them "stealth" properties within the body. The nanoparticles can also exhibit high selectivity for release of the drug (i.e., releasing minimal amounts of the drug before contact with a target cell). These properties are particularly desirable for drug delivery applications involving hydrophobic drugs such as Paclitaxel and Doxorubicin.

Herein, a drug can be any biologically active substance used in a medical treatment. Drugs include polymer drugs and non-polymer drugs. Polymer drugs include genes and proteins used in medical treatments. The nanoparticles can comprise both small molecular weight drugs in the size range from 100 g/mole to about 1,000 g/mole, as well as larger macromolecular drugs, such as peptide and protein drugs in the size range from about 1,000 daltons to about 100,000 daltons, and beyond.

The first block polymer and second block polymer can be biodegradable and/or biocompatible. The term "biodegradable" is defined by the American Society for Testing and Materials as a degradation caused by biological activity, especially by enzymatic action, leading to a significant change in the chemical structure of the material. For purposes herein, a material is "biodegradable" if it undergoes 60% biodegradation within 180 days in accordance with ASTM D6400. Herein, a material is "enzymatically biodegradable" if the material can be degraded (e.g., depolymerized) by a reaction catalyzed by an enzyme.

A "biocompatible" material is defined herein as a material capable of performing with an appropriate host response in a specific application.

The first block polymer comprises i) a poly(ethylene oxide) block referred to as the "first PEO block" and ii) a polycarbonate (PC) block, referred to as the "first PC block". The first PC block comprises a carbonate repeat unit having an aliphatic carbonate backbone portion and a side chain linked to the backbone portion. The side chain includes an aromatic nitrogen-containing heterocycle. This repeat unit is referred to as the "first repeat unit." The first PEO block can have a degree of polymerization of about 80 to about 200. The terminus of the poly(ethylene oxide) block can be any suitable end group (e.g., methyl, as in mono-methyl poly (ethylene glycol) (mPEG-OH)).

The first block polymer has a structure in accordance with formula (1):

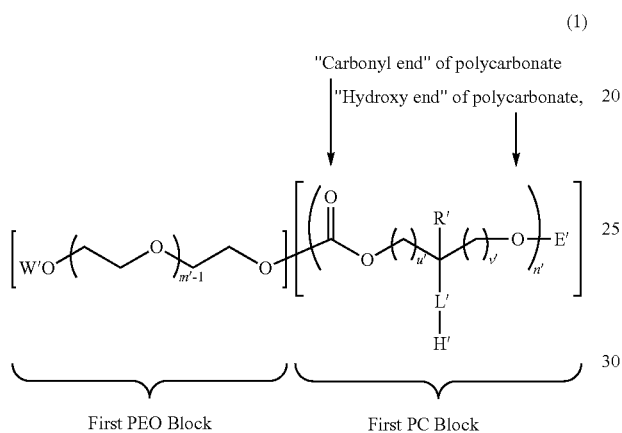

wherein
u' is a positive integer from 0 to 6,
v' is a positive integer from 0 to 6,
u' and v' cannot both be zero,
n' is a positive number of 2 to about 50,
m' is a positive number of about 80 to about 200,
E' is a monovalent end group selected from the group consisting of hydrogen and functional groups comprising 1 or more carbons,
H' is a functional group selected from the group consisting of non-charged aromatic nitrogen-containing heterocycles, hydrosalts of aromatic nitrogen-containing heterocycles, sulfobetaine adducts of aromatic nitrogen-containing heterocycles, and combinations thereof,
L' is a divalent linking group comprising 2 or more carbons,
R' is a monovalent radical selected from the group consisting of hydrogen and alkyl groups comprising 1 to 6 carbons, and
W' is a monovalent end group comprising 1 to 10 carbons.

For clarity the "carbonyl end" and the "hydroxy end" of the polycarbonate chain are labeled in the structure of formula (1). Preferably, E' is linked to the hydroxy end of the polycarbonate chain and the PEO block is linked to the carbonyl end of the polycarbonate chain, as shown.

In an embodiment, u' is 1, v' is 1, E' is hydrogen, R' is methyl, and W' is methyl.

The aromatic nitrogen-containing heterocycle H' is indirectly covalently linked to the polycarbonate backbone by way of linking group L'. Non-limiting examples of aromatic nitrogen containing heterocycles H' include substituted and/or unsubstituted pyrroles, indoles, isoindoles, imidazoles, benzimidazoles, pyrazoles, indazoles, pyridines, quinolines, isoquinolines, pyrazines, quinoxalines, pyrimidines. In an embodiment, the nitrogen-containing heterocycle is selected from the group consisting of imidazole, pyridine, and combinations thereof. First repeat units comprising different nitrogen-containing heterocycles can be present in the first block polymer singularly or in combination.

In an embodiment, the first repeat unit comprising H' is non-charged. The non-charged form of the aromatic nitrogen-containing heterocycle is the free base form of the heterocycle.

Hydrosalts of aromatic nitrogen-containing heterocycles refer to protonated forms of the nitrogen-containing heterocycle in ionic association with a negative-charged counterion (e.g., chloride, bromide, iodide). First repeat units comprising different hydrosalts of aromatic nitrogen-containing heterocycles can be present in the first block polymer singularly or in combination.

Non-limiting examples of sulfobetaine adducts of nitrogen-containing heterocycles include:

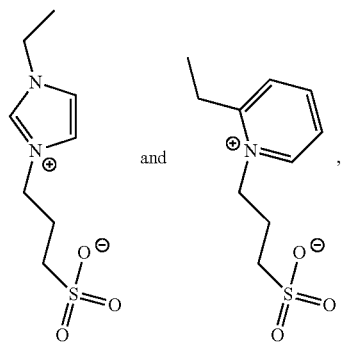

which can be prepared by reacting a corresponding aromatic amine with propane sultone. First repeat units comprising different sulfobetaine adducts of aromatic nitrogen-containing heterocycles can be present in the first block polymer singularly or in combination.

The first block polymer preferably contains no quaternary nitrogen other than a sulfobetaine adduct. In an embodiment, the first block polymer excludes quaternary nitrogen other than a sulfobetaine adduct.

The first repeat unit bearing H' has a structure in accordance with formula (2):

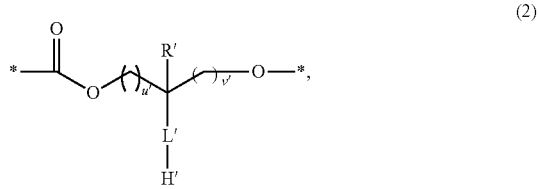

wherein
u' is a positive integer from 0 to 6,
v' is a positive integer from 0 to 6,
u' and v' cannot both be zero,
H' is a functional group selected from the group consisting of non-charged aromatic nitrogen-containing heterocycles, hydrosalts of aromatic nitrogen-containing heterocycles, sulfobetaine adducts of aromatic nitrogen-containing heterocycles, and combinations thereof, L' is a divalent linking group comprising 2 or more carbons, and R' is a monovalent radical selected from the group consisting of hydrogen and alkyl groups comprising 1 to 6 carbons.

The starred bonds of formula (2) represent attachment points to other portions of the polycarbonate chain and/or end groups.

More specific first repeat units of formula (2) have a structure in accordance with formula (3):

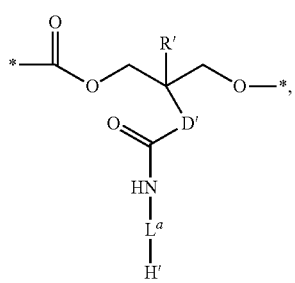
(3)

wherein

D' is a single bond, divalent oxygen (*—O—*), or divalent nitrogen (*—NH—*),

H' is a functional group selected from the group consisting of non-charged aromatic nitrogen-containing heterocycles, hydrosalts of aromatic nitrogen-containing heterocycles, sulfobetaine adducts of aromatic nitrogen-containing heterocycles, and combinations thereof, $L^a$ is a divalent linking group comprising 1 or more carbons, and R' is a monovalent radical selected from the group consisting of hydrogen and alkyl groups comprising 1 to 6 carbons.

Non-limiting examples of first repeat units of formula (3) include:

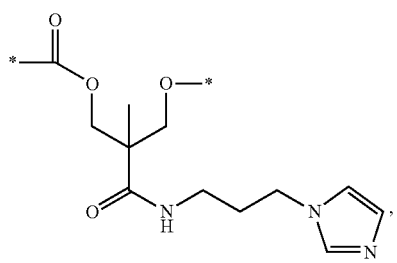,

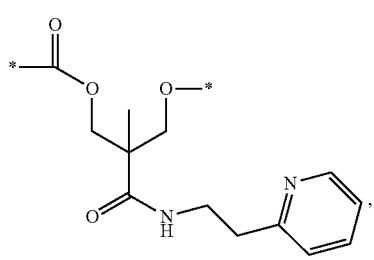,

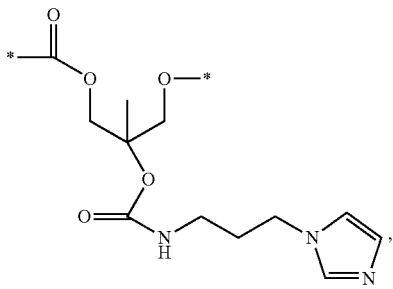,

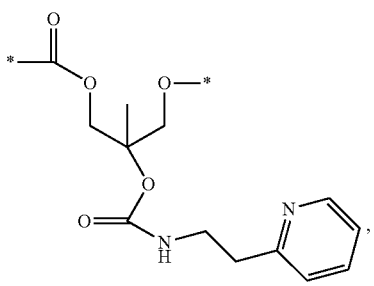,

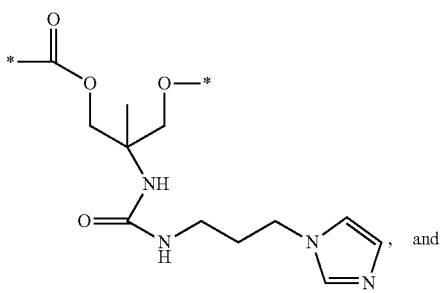, and

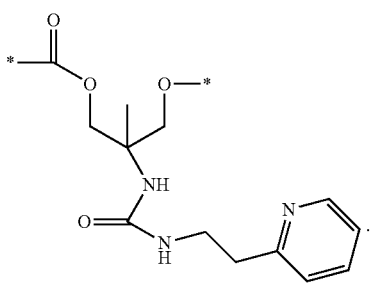.

The first block polymer can comprise repeat units of formula (3) singularly or in combination.

The second block polymer comprises i) a poly(ethylene oxide) block, referred to as the "second PEO block", and ii) a polycarbonate block, referred to as the "second PC block." The second PC block comprises a carbonate repeat unit having an aliphatic carbonate backbone portion and a side chain linked to the backbone portion. The side chain includes a catechol group. This repeat unit is referred to as the "second repeat unit." The catechol group of the second repeat unit is indirectly covalently bonded to the polycarbonate backbone by way of the side chain. The second PEO block can have a degree of polymerization of about 80 to about 200. The terminus of the second PEO block can be any suitable end group (e.g., methyl).

The second block polymer has a structure in accordance with formula (4):

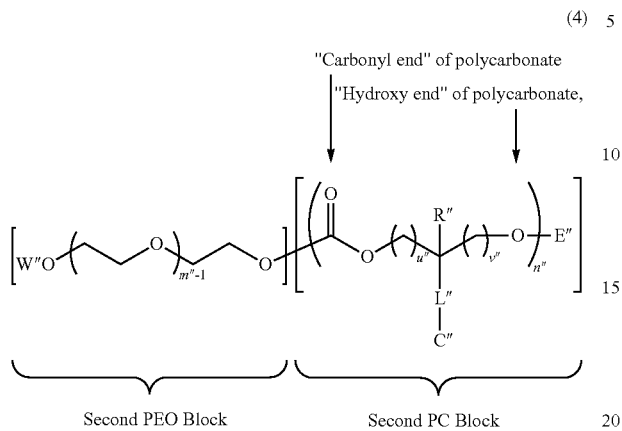

(4)

"Carbonyl end" of polycarbonate
"Hydroxy end" of polycarbonate,

Second PEO Block   Second PC Block wherein
u" is a positive integer from 0 to 6,
v" is a positive integer from 0 to 6,
u" and v" cannot both be zero,
n" is a positive number of 2 to about 50,
m" is a positive number of about 80 to about 200,
E" is a monovalent end group selected from the group consisting of hydrogen and functional groups comprising 1 or more carbons,
C" is a moiety comprising a catechol group,
L" is a divalent linking group comprising 2 or more carbons,
R" is a monovalent radical selected from the group consisting of hydrogen and alkyl groups comprising 1 to 6 carbons, and
W" is a monovalent end group comprising 1 to 10 carbons.

The carbonyl end and the hydroxy end of the polycarbonate chain are labeled in formula (4). In an embodiment, u" is 1, v" is 1, E" is hydrogen, and R" is methyl.

The second repeat unit of the second PC block that bears a catechol group has a structure in accordance with formula (5):

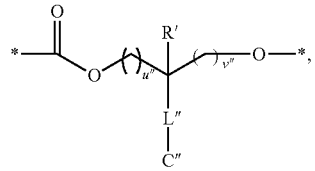

(5)

wherein
u" is a positive integer from 0 to 6,
v" is a positive integer from 0 to 6,
u" and v" cannot both be zero,
C" is a moiety comprising a catechol group,
L" is a divalent linking group comprising 2 or more carbons, and
R' is a monovalent radical selected from the group consisting of hydrogen and alkyl groups comprising 1 to 6 carbons.

The starred bonds of formula (5) represent attachment points to other portions of the polycarbonate chain and/or end groups.

A more specific carbonate repeat unit of formula (5) has a structure in accordance with formula (6):

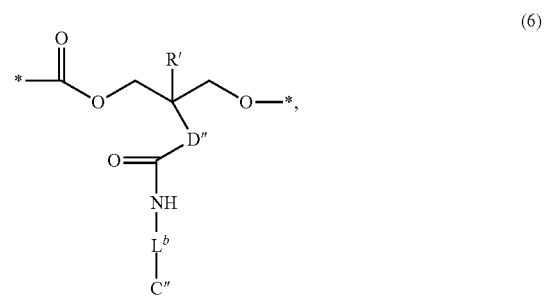

(6)

wherein
D" is a single bond, divalent oxygen (*—O—*), or divalent nitrogen (*—NH—*),
C" is a moiety comprising a catechol group,
$L^b$ is a divalent linking group comprising 1 or more carbons, and
R" is a monovalent radical selected from the group consisting of hydrogen and alkyl groups comprising 1 to 6 carbons.

Non-limiting examples of repeat units of formula (6) include:

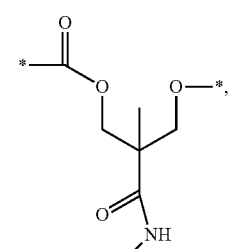

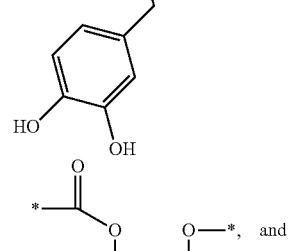

and

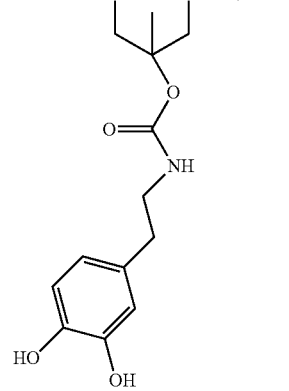

-continued

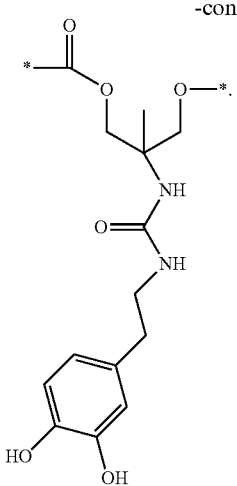

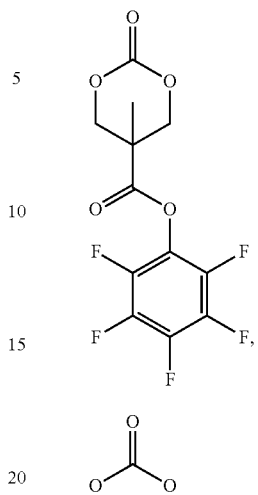
(MTC-OC6F5)

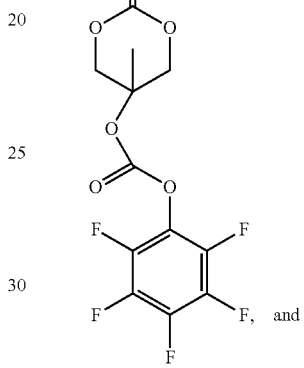
(TMCPFP)

, and

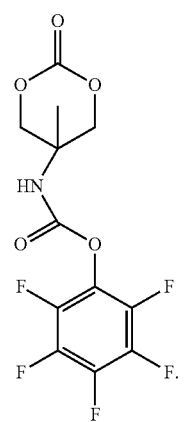
(TMCUPFP)

The second block polymer can comprise repeat units of formula (6) singularly or in combination.

Ring Opening Polymerization (ROP)

The first block polymer and the second block polymer are preferably prepared by a process that includes an organocatalyzed ring opening polymerization of a cyclic carbonate monomer bearing a pendant pentafluorophenyl ester, pentafluorophenyl carbonate, or pentafluorophenyl carbamate group that is capable of nucleophilic displacement by a primary amine to form an amide, carbamate, or urea group, respectively, after the ROP.

An exemplary ROP comprises agitating a reaction mixture comprising i) a solvent, ii) a first cyclic carbonate monomer bearing a pendant active pentafluorophenyl ester, pentafluorophenyl carbonate group, or pentafluorophenyl carbamate group iii) a catalyst, iv) a mono-nucleophilic polyether initiator, and v) an optional base accelerator, thereby forming an initial block polymer comprising a polyether block and a polycarbonate block, the polycarbonate block having an active pendant pentafluorophenyl group. The initial block polymer comprises an active end group (hydroxyl group) capable of initiating another ROP. The active end group can be end capped (e.g., by acylating the hydroxyl group with acetic anhydride) to stabilize the polycarbonate chain (e.g., from backbiting chain scission reactions) and/or to introduce desirable end group functionality (e.g., a cell recognition group). In an embodiment, the hydroxy end of the polycarbonate block of the initial block polymer is not capped.

The initial block polymer can be a common intermediate in the preparations of the first block polymer and second block polymer. In this instance, treating the initial block polymer with a first compound comprising i) a nucleophilic group capable of displacing the active pentafluorophenyl group and ii) an aromatic nitrogen-containing heterocycle produces the first block polymer. In a separate reaction, treating the initial block polymer with a second compound comprising i) a nucleophilic group capable of displacing the active pentafluorophenyl group and ii) a catechol group (e.g., dopamine) produces the second block polymer.

Cyclic Carbonyl Monomers

Non-limiting examples of cyclic carbonate monomers bearing active pentafluorophenyl groups include:

MTC-OC6F5 has a pendant pentafluorophenyl ester capable of reacting with a primary amine to form an amide. TMCPFP has a pendant pentafluorophenyl carbonate group capable of reacting with a primary amine to form a carbamate (urethane). TMCUPFP has a pendant pentafluorophenyl carbamate group capable of reacting with a primary amine to form a urea. The foregoing cyclic carbonates can be used singularly or in combination.

The ROP reaction mixture can include one or more additional cyclic carbonyl monomers selected from the group consisting of cyclic carbonate monomers, cyclic ester monomers, and combinations thereof. These diluent monomers can be employed to adjust hydrophobicity or other properties of the first block polymer. Thus, the polycarbonate block of the initial block polymer, the first block polymer, and/or the second block polymer can be a homopolymer of the first cyclic carbonate monomer bearing an active pentafluorophenyl group or a random copolymer of the first cyclic carbonate monomer. For example, the copolymer can be a polycarbonate copolymer prepared from a mixture of cyclic carbonate monomers, or a polyestercarbonate copolymer prepared from a mixture of cyclic carbonate and cyclic ester monomers.

Exemplary diluent cyclic carbonyl monomers for generating the copolymers include the cyclic carbonate and cyclic ester monomers listed in Table 1.

TABLE 1

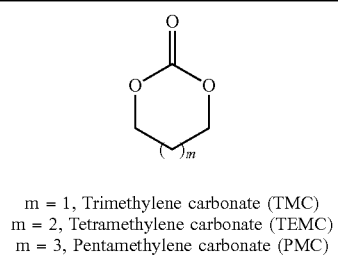

m = 1, Trimethylene carbonate (TMC)
m = 2, Tetramethylene carbonate (TEMC)
m = 3, Pentamethylene carbonate (PMC)

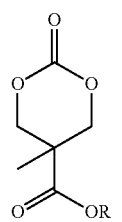

R = methyl (MTCOMe)
R = t-butyl (MTCO$^t$Bu)
R = ethyl (MTCOEt)

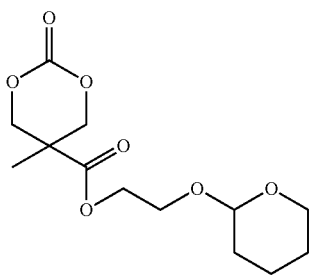 [SMILES: CC1(C(=O)OCCOC2CCCCO2)COC(=O)OC1]

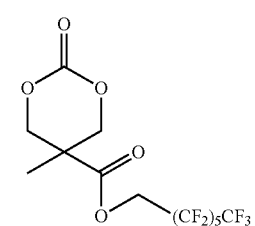

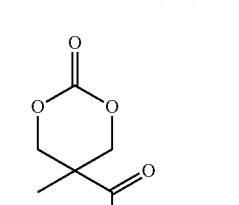

(MTCTFE)

TABLE 1-continued

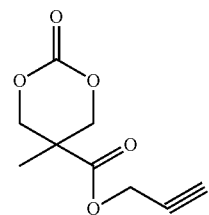

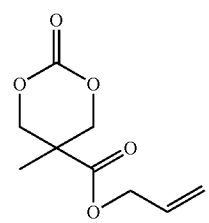

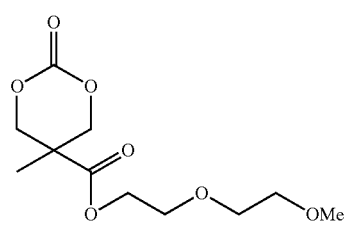 [SMILES: COCCOCCOC(=O)C1(C)COC(=O)OC1]

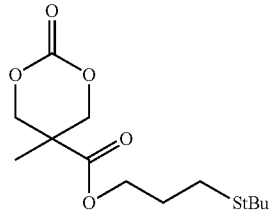

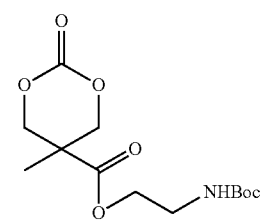 [SMILES: CC(C)(C)OC(=O)NCCOC(=O)C1(C)COC(=O)OC1]

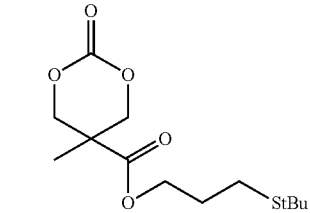

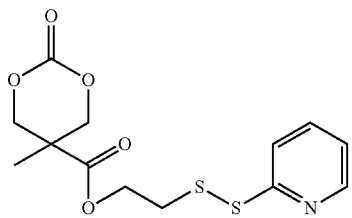 [SMILES: CC1(C(=O)OCCSSc2ccccn2)COC(=O)OC1]

TABLE 1-continued
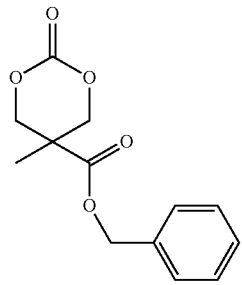 [SMILES: CC1(C(=O)OCc2ccccc2)COC(=O)OC1]
(MTCOBn)
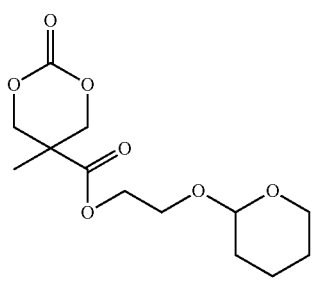 [SMILES: CC1(C(=O)OCCOC2CCCCO2)COC(=O)OC1]
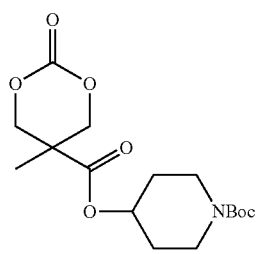 [SMILES: CC(C)(C)OC(=O)N1CCC(OC(=O)C2(C)COC(=O)OC2)CC1]
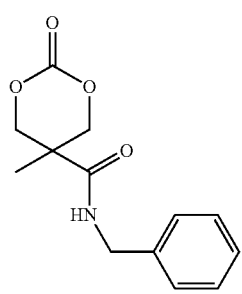 [SMILES: CC1(C(=O)NCc2ccccc2)COC(=O)OC1]
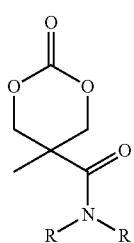
R = methyl
R = iso-propyl
TABLE 1-continued
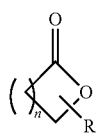
R = H; n = 1: beta-Propiolactone (b-PL)
R = H; n = 2: gamma-Butyrolactone (g-BL)
R = H; n = 3: delta-Valerolactone (d-VL)
R = H; n = 4: epsilon-Caprolactone (e-CL)
R = CH3; n = 1: beta-Butyrolactone (b-BL)
R = CH3; n = 2: gamma-Valerolactone (g-VL)
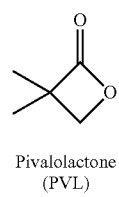
Pivalolactone
(PVL)
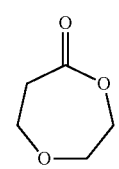
1,5-Dioxepan-2-one
(DXO)
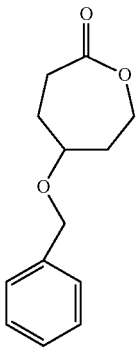 [SMILES: O=C1CCC(OCc2ccccc2)CCO1]
5-(Benzyloxy)oxepan-2-one
(BXO)
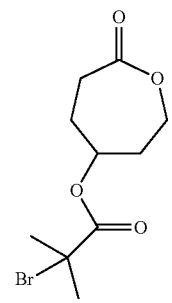
7-Oxooxepan-4-yl 2-bromo-2-methylpropanoate
(BMP-XO)

TABLE 1-continued

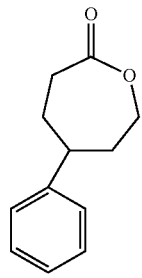 [SMILES: O=C1CCC(c2ccccc2)CCO1]

5-Phenyloxepan-2-one
(PXO)

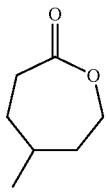

5-Methyloxepan-2-one
(MXO)

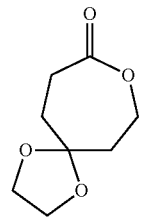 [SMILES: O=C1CCC2(CCO1)OCCO2]

1,4,8-Trioxa(4,6)spiro-9-undecane
(TOSUO)

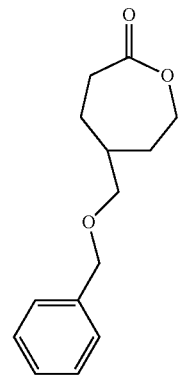 [SMILES: O=C1CCC(COCc2ccccc2)CCO1]

5-(Benzyloxymethyl)oxepan-2-one
(BOMXO)

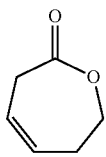

(Z)-6,7-Dihydrooxepin-2(3H)-one
(DHXO)

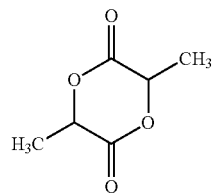

D-Lactide (DLA)
L-Lactide (LLA) or
racemic Lactide, 1:1 D:L forms (DLLA)

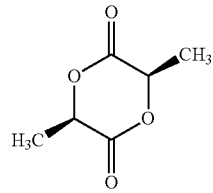

meso-Lactide (MLA)
(two opposite centers of asymmetry
R and S)

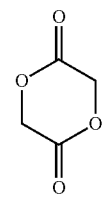

Glycolide
(GLY)

Initiators

ROP initiators generally include nucleophiles such as alcohols, amines and thiols. The initiators for the ROPs used to prepare the first block polymer and the second block polymer are preferably mono-nucleophilic polyether initiators. The first block polymer and the second block polymer can be prepared using the same polyether initiator or different polyether initiators. More specific polyether initiators include mono-endcapped poly(ethylene glycol)s (PEGs) having one initiating site (e.g., a terminal hydroxy group). Alternatively, the polyether initiator can be a poly(ethylene oxide) having a terminal primary amine group, known in the trade as a PEG-amines. The polyether initiator can be a precursor to the first PEO block and/or the second PEO block.

A non-limiting example of a mono-endcapped poly(ethylene glycol) is mono-methyl poly(ethylene glycol) (mPEG-OH):

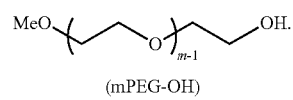

(mPEG-OH)

Subscript m can have a value in a range of about 50 to about 200, more preferably about 80 to about 150, and most preferably about 80 to about 120.

Catalysts

The ROP reaction mixture can comprise one or more catalysts. The ROP catalyst is added in a proportion of 1/20 to 1/40,000 moles relative to the cyclic carbonyl monomers, and preferably of 1/100 to 1/20,000 moles.

The catalyst for the ring opening polymerization of the cyclic carbonate monomer bearing the active pentafluorophenyl group is preferably a metal-free acid (e.g., triflic acid, $CF_3SO_3H$). Other metal-free ROP catalysts include hydrogen bond catalysts comprising at least one 1,1,1,3,3,3-hexafluoropropan-2-ol-2-yl (HFP) group:

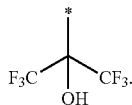

Singly-donating hydrogen bond catalysts have the formula (C-1):

$$R^2—C(CF_3)_2OH \quad (C-1).$$

$R^2$ represents a hydrogen or a monovalent radical having from 1 to 20 carbons, for example an alkyl group, substituted alkyl group, cycloalkyl group, substituted cycloalkyl group, heterocycloalkyl group, substituted heterocycloalklyl group, aryl group, substituted aryl group, or a combination thereof. Exemplary singly-donating hydrogen bonding catalysts are listed in Table 2.

TABLE 2

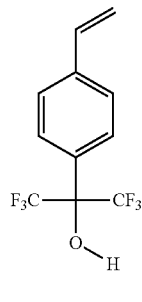

4-HFA-St

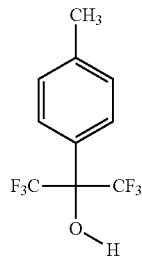

4-HFA-Tol

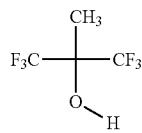

HFTB

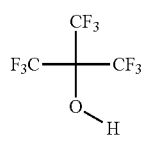

HFTB

TABLE 2-continued

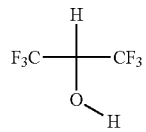

HFIP

Doubly-donating hydrogen bonding catalysts have two HFP groups, represented by the general formula (C-2):

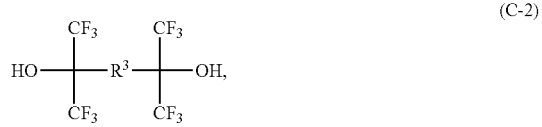

wherein $R^3$ is a divalent radical bridging group containing from 1 to 20 carbons, such as an alkylene group, a substituted alkylene group, a cycloalkylene group, a substituted cycloalkylene group, a heterocycloalkylene group, substituted heterocycloalkylene group, an arylene group, a substituted arylene group, or a combination thereof. Representative double hydrogen bonding catalysts of formula (C-2) include those listed in Table 3. In a specific embodiment, $R^2$ is an arylene or substituted arylene group, and the HFP groups occupy positions meta to each other on the aromatic ring.

TABLE 3

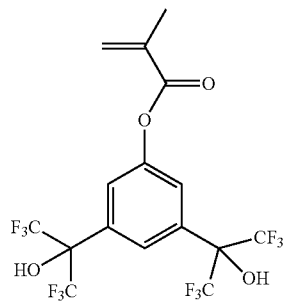 [SMILES: C=C(C)C(=O)Oc1cc(C(O)(C(F)(F)F)C(F)(F)F)cc(C(O)(C(F)(F)F)C(F)(F)F)c1]

3,5-HFA-MA

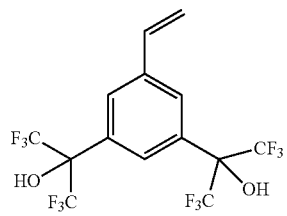

3,5-HFA-St

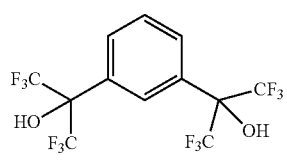

1,3-HFAB

TABLE 3-continued

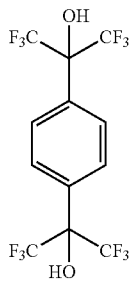

1,4-HFAB

Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha,alpha,alpha-trifluoromethacrylate, alpha-halomethacrylate, acrylamido, methacrylamido, norbornene, vinyl, vinyl ether, and other groups known in the art.

Another ROP catalyst is N-bis(3,5-trifluoromethyl)phenyl-N'-cyclohexyl-thiourea (TU):

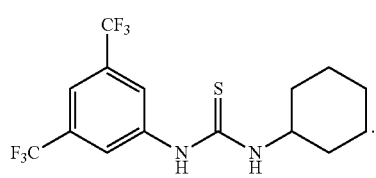
(TU)

The catalyst and the accelerator can be the same compound, such as 1,8-diazabicyclo[5.4.0]undec-7-ene (DBU).

Accelerators

ROPs conducted with an HFP-containing catalyst generally include an accelerator, in particular a nitrogen base. ROPs catalyzed by an acid catalyst (e.g., triflic acid) are performed without employing a nitrogen base accelerator.

Exemplary nitrogen base accelerators are listed below and include pyridine (Py), N,N-dimethylaminocyclohexane (Me₂NCy), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-1-propylphenyl(imidazol-2-ylidene (Im-3), 1,3-bis(1-adamantyl)imidazol-2-ylidene (Im-4), 1,3-di-1-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-1-propylphenyl)-4,5-dihydroimidazol-2-ylidene, 1,3-bis(2,6-di-1-propylphenyl)-4,5-dihydroimidazol-2-ylidene (Im-8) or a combination thereof, shown in Table 4.

TABLE 4

Pyridine
(Py)

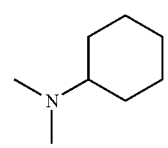

N,N-Dimethylaminocyclohexane
(Me2NCy)

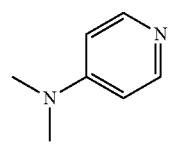

4-N,N-Dimethylaminopyridine
(DMAP)

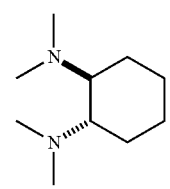

trans 1,2-Bis(dimethylamino)cyclohexane
(TMCHD)

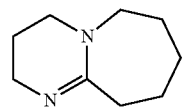

1,8-Diazabicyclo[5.4.0]undec-7-ene
(DBU)

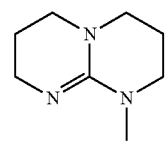

7-Methyl-1,5,7-triazabicyclo[4.4.0]dec-5-ene
(MTBD)

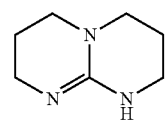

1,5,7-Triazabicyclo[4.4.0]dec-5-ene
(TBD)

TABLE 4-continued

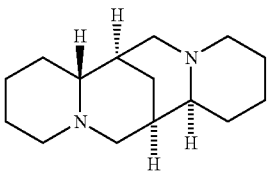 [SMILES: C1CCN2C[C@H]3C[C@H](CN4CCCC[C@@H]34)[C@H]2C1]

(-)-Sparteine
(Sp)

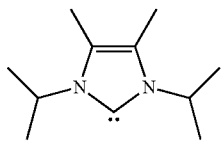

1,3-Bis(2-propyl)-4,5-dimethylimidazol-
2-ylidene
(Im-1)

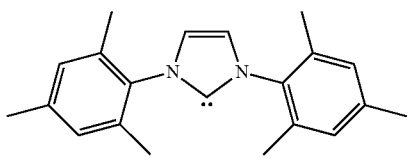

1,3-Bis(2,4,6-trimethylphenyl)imidazol-2-
ylidene
(Im-2)

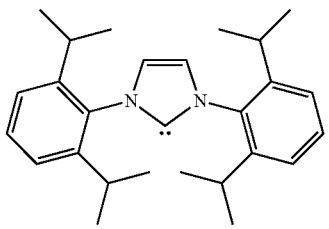

1,3-Bis(2,6-di-i-propylphenyl(imidazol-
2-ylidene
(Im-3)

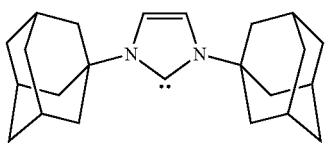

1,3-Bis(1-adamantyl)imidazol-2-yliden)
(Im-4)

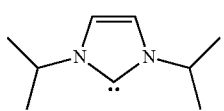

1,3-Di-i-propylimidazol-2-ylidene
(Im-5)

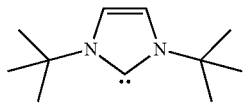

1,3-Di-t-butylimidazol-2-ylidene
(Im-6)

TABLE 4-continued

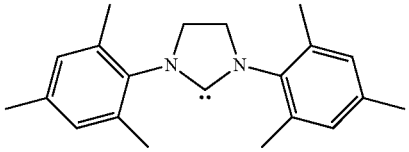

1,3-Bis(2,4,6-trimethylphenyl)-4,5-
dihydroimidazol-2-ylidene
(Im-7)

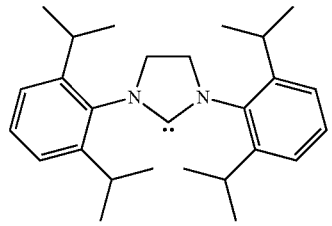

1,3-Bis(2,6-di-i-propylphenyl)-4,5-
dihydroimidazol-2-ylidene
(Im-8)

When used, the accelerator preferably has two or three nitrogens, each capable of participating as a Lewis base, as for example in the structure (−)-sparteine. Stronger bases generally improve the polymerization rate.

Solvents

Exemplary solvents for the ROP include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. The cyclic carbonyl monomer concentration in the reaction mixture is about 0.1 to 5 moles per liter, and more particularly about 0.2 to 4 moles per liter.

The ROP can be performed at about ambient temperature or higher, more specifically a temperature from 15° C. to about 50° C., and more particularly 20° C. to 30° C. Reaction times vary with solvent, temperature, agitation rate, pressure, and equipment, but in general the polymerizations are complete within 1 to 100 hours.

The polymerizations are conducted in an inert (i.e., dry) atmosphere and at a pressure of from 100 to 500 MPa (1 to 5 atm), more typically at a pressure of 100 to 200 MPa (1 to 2 atm). At the completion of the reaction, the solvent can be removed using reduced pressure.

When used, the nitrogen base accelerator is present in the ROP reaction mixture in an amount of 0.1 to 5.0 mol %, 0.1 to 2.5 mol %, 0.1 to 1.0 mol %, or 0.2 to 0.5 mol %, based on total moles of cyclic carbonyl monomer.

The amount of initiator is calculated based on the equivalent molecular weight per nucleophilic initiating group in the initiator (e.g., alcohol groups). The initiating groups are present in an amount of 0.001 to 10.0 mol %, 0.1 to 2.5 mol %, 0.1 to 1.0 mol %, and 0.2 to 0.5 mol %, based on total moles of cyclic carbonyl monomer. For example, if the molecular weight of the initiator is 100 g/mole and the initiator has 2 hydroxyl groups, the equivalent molecular weight per hydroxyl group is 50 g/mole. If the polymerization calls for 5 mol % hydroxyl groups per mole of monomer, the amount of initiator is 0.05×50=2.5 g per mole of monomer.

When an HFP catalyst is used, the HFP catalyst is present in the ROP reaction mixture in an amount of about 0.2 to 20 mol %, the nitrogen base accelerator is present in an amount of 0.1 to 5.0 mol %, and the hydroxyl groups of the initiator are present in an amount of 0.1 to 5.0 mol % based on the equivalent molecular weight per nucleophilic group of the initiator.

The first block polymer can have a number average molecular weight Mn as determined by size exclusion chromatography of at least 2500 g/mol, more specifically 4000 g/mol to 150000 g/mol, and even more specifically 10000 g/mol to 50000 g/mol. In an embodiment, the first block polymer has a number average molecular weight Mn of 10000 to 20000 g/mole. The first block polymer can have a narrow polydispersity index (PDI), generally from 1.01 to 1.35, more particularly 1.1 to 1.30, and even more particularly 1.1 to 1.25.

The second block polymer can have a number average molecular weight Mn as determined by size exclusion chromatography of at least 2500 g/mol, more specifically 4000 g/mol to 150000 g/mol, and even more specifically 10000 g/mol to 50000 g/mol. In an embodiment, the second block polymer has a number average molecular weight Mn of 10000 to 20000 g/mole. The second block polymer can have a narrow polydispersity index (PDI), generally from 1.01 to 1.35, more particularly 1.1 to 1.30, and even more particularly 1.1 to 1.25.

Micelle Formation

Herein, the terms "micelle" and "mixed micelle" does not include a drug. The first block polymer and the second block polymer can each form micelles when dissolved separately (alone) in water. The first block polymer and the second block polymer can form a mixed micelle when dissolved together in water, meaning a given mixed micelle particle comprises both polymers bound by at least non-covalent interactions.

Prior to drug loading, the mixed micelles can have an average particle size (average circular diameter) of about 20 nm to about 500 nm, and a polydispersity of about 0.06 to about 0.50. Prior to drug loading, the mixed micelles can induce 0% to 20%, 0% to 15%, 0% to 10%, 0% to 5%, 0% to 2%, or more particularly 0% to 1% cytotoxicity. In an embodiment, the mixed micelles exhibit no cytotoxicity.

Drug-Loaded Mixed Micelles (Nanoparticles)

The mixed micelles can be loaded with a drug, more specifically a hydrophobic drug, by combining with agitation an aqueous solution containing the mixed micelles with a second solution containing a drug dissolved in a water miscible organic solvent (e.g., N,N-dimethyl acetamide (DMAc)). Removing the organic solvent (e.g., by dialysis) from the resulting mixture produces a drug-loaded mixed micelle, or simply nanoparticle. A given nanoparticle comprises, in contact together, the drug, the first block polymer, and the second block polymer bound at least by non-covalent interactions. The nanoparticles can be isolated as water-dispersible solid particles by removing the water (e.g., by lyophilization). In an embodiment the drug is Doxorubicin.

The catechol group of the nanoparticle can potentially undergo spontaneous oxidation and/or polymerization based on known catechol reactions (e.g., dopamine readily forms polydopamine when disposed on a substrate surface). No attempt was made in the examples further below to either minimize the potential side reactions of the catechol group or characterize the chemical byproducts formed. Therefore, the catechol group of the nanoparticles can potentially exist as a catechol, an oxidized catechol (quinone), a polymerized catechol, polymerized quinone, or a combination of any of the foregoing functionalities. Given the potential catechol side reactions, the nanoparticles can also potentially include crosslinked forms of the second block polymer resulting from coupling of the catechol groups. No attempt was made to characterize the extent of the crosslinking. Due to the possible complexity of the resulting chemical structure of the nanoparticle, the nanoparticle compositions are described based on the feed materials used to prepare the nanoparticles unless otherwise indicated.

The nanoparticles preferably have an average particle size (average circular diameter) of about 20 nm to about 700 nm at a pH of 5.0 to 8.0. The nanoparticles can have a size polydispersity of about 0.2 to about 0.5.

Further disclosed is a method of treating a cell, comprising contacting the cell with an aqueous mixture comprising the disclosed nanoparticles. The biologically active cargo can comprise a single drug or a mixture of drugs. Cells can be contacted in vitro, ex vivo, or in vivo.

The sum of the weight percent (wt %) of the drug, the wt % of the first block polymer, and the wt % of the second block polymer of the nanoparticles equals 100 wt %, where weight percent (wt %) is based on total dry weight of the nanoparticles. Given these conditions, the nanoparticles can comprise the drug in an amount of about 0.1 wt % to about 30 wt %, and more particularly about 3.0 wt % to about 20 wt % based on total dry weight of the nanoparticles.

The nanoparticles can comprise the first block polymer in an amount of about 10 wt % to about 90 wt %, preferably about 30 wt % to about 60 wt % based on total dry weight of the nanoparticles.

The nanoparticles can comprise the second block polymer in an amount of about 10 wt % to about 90 wt %, preferably about 30 wt % to about 60 wt % based on total dry weight of the nanoparticles.

Drugs

Exemplary protein drugs include peptide hormones such as insulin, glucagon, parathyroid hormone, calcitonin, vasopression, renin, prolactin, growth hormone, the gonadotropins including chorionic gonadotropin, follicle stimulating hormone, thyroid stimulating hormone and leutenizing hormone; physiologically active enzymes such as transferases, hydrolases, lyases, isomerases, phosphatases, glycosidases; superoxide dismutase, factor VIII, plasminogen activators; and other therapeutic agents including protein factors such as epidermal growth factor, insulin-like growth factor, tumour necrosis factor, transforming growth factors, fibroblast growth factors, patelet-derived growth factors, erythropoietin, colony stimulating factors, bone morphogenetic proteins, interleukins and interferons. Exemplary non-protein macromolecules include polysaccharides, nucleic acid polymers, and therapeutic secondary metabolites including plant products such as vinblastine, vincristine, taxol and the like.

Other drugs include Aspirin, Diflunisal, Diclofenac, Aceclofenac, Acemetacin, Etodolac, Indometacin, Sulindac, Tolmetin, Ibuprofen, Carprofen, Fenbufen, Fenoprofen, Flurbiprofen, Ketoprofen, Ketorolac, Loxoprofen, Naproxen, Oxaprozin, Tiaprofenic acid, Suprofen, Mefenamic acid, Meclofenamic acid, Lumiracoxib, Oxyphenbutazone, Piroxicam, Lornoxicam, Meloxicam, and Tenoxicam. Steroidal Anti-Inflammatory Drugs include Hydrocortisone, Prednisone, Prednisolone, Methylprednisolone, Dexamethasone, Betamethasone, Triamcinolone, Beclometasone, Fludrocortisone acetate, and Aldosterone. Chemotherapeutic drugs include Doxorubicin and DNA alkylating Agents such as Melphalan, Chlorambucil, Dacarbazine, Temozolomide, and Streptozotocin. Antimetabolite drugs include Methotrexate, Pemetrexed, Raltitrexed, Tioguanine, Fludarabine, Pentostatin, Cladribine, Floxuridine, and Gemcitabine. Alkaloid drugs include Vincristine, Vinblastine, Vinorelbine, Vindesine, and Topoisomerase. Inhibitors include Etoposide, Teniposide, Irinotecan, and Topotecan. Taxanes include Paclitaxel and Docetaxel. Anticoagulants include Warfarin, Acenocoumarol, Phenprocoumon, Argatroban, and Ximelagatran.

Still other exemplary commercially available drugs include 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone Acetate, Dexamethasone Sodium Phosphate Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, *Erwinia* L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar, Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexylen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan Idamycin®, Idarubicin, Ifex®, IFN-alpha Ifosfamide, IL-11 IL-2 Imatinib mesylate, Imidazole Carboxamide Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, K Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Oraped®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRONT™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a) Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, and Zometa.

No restriction is placed on the type of cell that can be treated with the above-described nanoparticles. In particular, the cells can be eukaryotic cells, mammalian cells, and more particularly rodent and/or human cells. The cells can be derived from various tissues, including extraembryonic or embryonic stem cells, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, dendritic cells, neurons, glia, mast cells, blood cells and leukocytes (e.g., erythrocytes, megakaryotes, lymphocytes, such as B, T and natural killer cells, macrophages, neutrophils, eosinophils, basophils, platelets, granulocytes), epithelial cells, keratinocytes, chondrocytes, osteoblasts, osteoclasts, hepatocytes, and cells of the endocrine or exocrine glands, as well as sensory cells.

The nanoparticles can be used as non-viral transfection vectors. The target gene is not limited to any particular type of target gene or nucleotide sequence. For example, the target gene can be a cellular gene, an endogenous gene, an oncogene, a transgene, or a viral gene including translated and non-translated RNAs. Exemplary possible target genes include: transcription factors and developmental genes (e.g., adhesion molecules, cyclin-dependent kinase inhibitors, Wnt family members, Pax family members, Winged helix family members, Hox family members, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, ERBB2, ETSI, ETV6, FGR, FOS, FYN, HCR, HRAS, JUN, KRAS, LCK, LYN, MDM2, MLL, MYB, MYC, MYCLI, MYCN, NRAS, PIMI, PML, RET, SKP2, SRC, TALI, TCL3, and YES); tumor suppressor genes (e.g., APC, BRAI, BRCA2, CTMP, MADH4, MCC, NF1, NF2, RBI, TP53, and WTI); and enzymes (e.g., ACP desaturases and hydroxylases, ADP-glucose pyrophorylases, ATPases, alcohol dehydrogenases, amylases, amyloglucosidases, catalases, cyclooxygenases, decarboxylases, dextrinases, DNA and RNA polymerases, galactosidases, glucose oxidases, GTPases, helicases, integrases, insulinases, invertases, isomerases, kinases, lactases, lipases, lipoxygenases, lysozymes, peroxidases, phosphatases, phospholipases, phosphorylases, proteinases and peptidases, recombinases, reverse transcriptases, telomerase, including RNA and/or protein components, and topoisomerases).

Poly(sulfobetaine)s are poly-zwitterions that can potentially mimic phosphatidylcholine-based biomembranes. These polymers are generally highly hygroscopic, and their chains tend to be surrounded by a sheath of water molecules when dissolved in aqueous media, which can increase resistance to cell adhesion and antibody opsonization, as is the case with poly(ethylene glycol) (PEG) systems, known for their in vivo stealth properties. The disclosed polycarbonate-based poly(sulfobetaine)s, which utilize a low molecular weight PEO block, is advantaged over prior PEG-based systems due to its in vivo biodegradability, which can lower bioaccumulation that may lead to toxicity issues. Therefore, the poly(sulfobetaine)s synthesized herein are attractive as biodegradable PEG alternatives in applications such as biocompatible and hemocompatible anti-fouling materials as well as protein-delivery agents.

Also disclosed are quaternized derivatives of the polycarbonates bearing pendant N-heterocycles. The quarternization of the N-heterocycle with alkylating agents yields highly water soluble polyelectrolytes. The resulting quaternized N-heterocycle polymer can potentially serve as a biodegradable antimicrobial agent, as positively-charged side chains can disrupt anionic bacterial cell membranes. The modular nature of the synthesis allows for numerous different alkylating agents to be employed (e.g., methyl iodide, benzyl bromide, or other alkyl halides of varying chain lengths).

Also disclosed are partially quaternized derivatives of the polycarbonates bearing the pendant N-heterocycles. Partial quaternization using sub-stoichiometric amounts of alkylating agent can potentially produce polymers that may be useful for RNA/DNA transfection via the "proton-sponge" effect. In principle, the polycarbonate with its positively-charged pendant rings would bind to a negative-charged polynucleotide strand via coulombic attraction, and the resulting 'polyplex' would enter a cell via endocytosis. The substantial buffering capacity of the polymer conferred by its non-quaternized and non-charged pendant N-heterocycles may not only inhibit the action of lysosomal nucleases during intracellular trafficking, but potentially also sequester protons (like a "sponge") supplied by the v-ATPase proton pump. Prolonged proton sequestration can alter the osmolarity of the endosome to the point where it lyses, thereby releasing the encapsulated poly/oligonucleotide cargo for delivery to the cell nucleus. As such, the partially quaternized N-heterocycle-containing polycarbonates offer the possibility of a biodegradable gene delivery vehicle.

The following examples illustrate methods of forming block polycarbonates bearing pendant N-heterocycles, the formation of mixed micelles with block polycarbonates bearing catechol groups, and methods of formation of the drug-loaded mixed micelles (nanoparticles). The examples also disclose methods of functionalizing the pendant N-heterocycles, including formation of sulfobetaine derivatives by reaction with a sultone. The examples demonstrate that a single heterocycle-containing polycarbonate can serve as a common precursor for more complex functionalized polymers. Structural diversity can be incorporated via the choice of cyclic carbonyl monomers, choice of N-heterocycle compounds grafted onto the initial polycarbonate, and the type of chemical modification on the pendant N-heterocycle.

Purification of the polymers can be achieved by precipitation, washing, sonication, centrifugation, and combinations thereof.

EXAMPLES

Materials used in the following examples are listed in Table 5.

TABLE 5

| ABBREVIATION | DESCRIPTION | SUPPLIER |
|---|---|---|
| MTC-OC6F5 | 5-methyl-5-pentafluorophenyloxycarbonyl-1,3-dioxan-2-one | Central Glass |
| MTC-OEt | 5-methyl-5-ethyloxycarbonyl-1,3-dioxan-2-one | Prepared below |
| Bis-MPA | 2,2-Bis(methylol)propionic acid | Sigma-Aldrich |
| DCM | Dichloromethane | Sigma Aldrich |
| | AMBERLYST 15 | Sigma Aldrich |
| Triflic Acid | Trifluoromethanesulfonic acid | Sigma Aldrich |
| APIm | 1-(3-Aminopropyl)imidazole | Sigma-Aldrich |
| mPEG-OH | Monomethyl poly(ethylene glycol), Mn = 5000 | Sigma-Aldrich |
| Tyramine | 4-Hydroxyphenethylamine | Sigma-Aldrich |
| Dopamine •HCl | Dopamine hydrochloride | Sigma-Aldrich |
| RPMI-1640 | Roswell Park Memorial Institute-1640 | PAA (Singapore) |
| PBS | Phosphate Buffered Saline | BD Diagnostics (Singapore) |
| DOX | Doxorubicin | Sigma Aldrich |

Herein, Mn is the number average molecular weight, Mw is the weight average molecular weight, and MW is the molecular weight of one molecule.

MTC-C6F5 was obtained from Central Glass and purified by crystallizing twice from a mixture of ethyl acetate and hexanes. Anhydrous solvents were dried using activated alumina columns and stored over molecular sieves (3 Å). All other materials were purchased from Sigma-Aldrich and used as received.

$^1$H NMR spectra were acquired on a Bruker Avance 400 instrument at 400 MHz. Gel permeation chromatography (GPC) was performed in tetrahydrofuran (THF) using a Waters system equipped with four 5-micrometer Waters columns (300 mm×7.7 mm) connected in series with increasing pore size (100, 1000, 105, and 106 angstroms), a Waters 410 differential refractometer, and a 996 photodiode array detector. The system was calibrated using polystyrene standards. GPC analysis was also performed in N,N-dimethylformamide (DMF) spiked with 0.01 M LiBr using a Waters system equipped with two Agilent PolyPore columns (300 mm×7.5 mm) connected in series, a Waters 410 differential refractometer. The system was calibrated with poly(methyl methacrylate) standards.

Monomer Synthesis

Preparation of 5-methyl-5-ethyloxycarbonyl-1,3-dioxan-2-one (MTC-OEt) (MW 188.2)

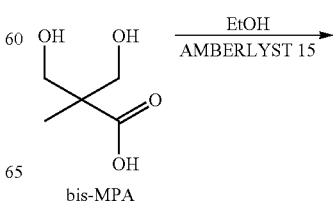

bis-MPA

-continued

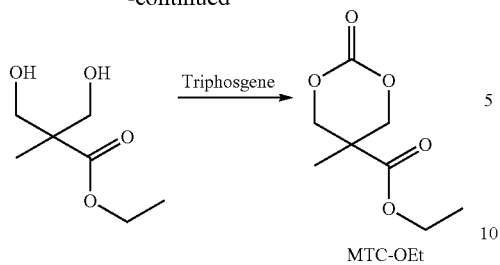

MTC-OEt

MTC-OEt

(i) bis-MPA (22.1 g, 0.165 mol) was added to ethanol (150 mL) containing AMBERLYST 15 (6.8 g) and refluxed overnight. The resins were then filtered out and the filtrate was evaporated. Methylene chloride (DCM, 200 mL) was added to the resulting viscous liquid was filtered. The filtrate was dried over MgSO4 and evaporated, yielding ethyl 2,2-bis(methylol)propionate as a clear and colorless liquid (24.3 g, 91%). $^1$H NMR (400 MHz, CDCl$_3$, 22° C.): delta=4.09 (q, 2H, —OCH$_2$CH$_3$), 3.74 (d, 2H, —CH$_2$OH), 3.57 (d, 2H, —CH$_2$OH), 1.18 (t, 3H, —OCH$_2$CH$_3$), 0.98 (s, 3H, —CH$_3$). (ii) A solution of triphosgene (11.7 g, 0.039 mol) in DCM (150 mL) was added dropwise to a DCM solution (150 mL) of ethyl 2,2-bis(methylol)propionate (12.6 g, 0.078 mol) and pyridine (39 mL, 0.47 mol) over 30 minutes at −75° C. with dry ice/acetone under nitrogen atmosphere. The reaction mixture was stirred for another 2 hours under chilled conditions and then allowed to warm to room temperature. The reaction was quenched by addition of saturated aqueous NH$_4$Cl (75 mL), after which the organic layer was washed with 1 M aqueous HCl (3×100 mL), saturated aqueous NaHCO$_3$ (1×100 mL), dried over MgSO4, filtered and evaporated. The residue was recrystallized from ethyl acetate to give MTC-OEt as white crystals (8.0 g, 55%). $^1$H NMR (400 MHz, CDCl$_3$, 22° C.): delta=4.67 (d, 2H, —CH$_2$OCOO), 4.25 (q, 2H, —OCH$_2$CH$_3$), 4.19 (d, 2H, —CH$_2$OCOO), 1.30 (s, 3H, —CH$_3$), 1.27 (t, 3H, —OCH$_2$CH$_3$)

In the following polymer preparations, the polycarbonate chain is not end capped at the hydroxyl end. The carbonyl end of the polycarbonate backbone is linked to a fragment derived from the initiator for the ring opening polymerization (ROP).

Preparations of Active Pentafluorophenyl Ester Containing Polymers.

The fluorinated polymers have a name beginning with "F".

Example 1

Preparation of F-1 (Degree of Polymerization (DP)=100)

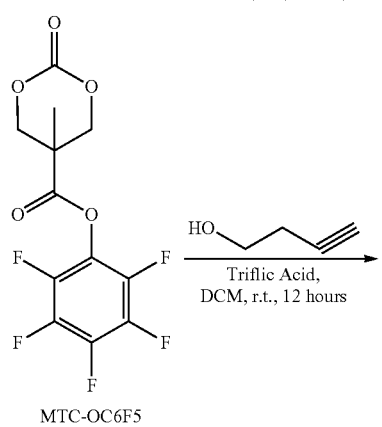

MTC-OC6F5

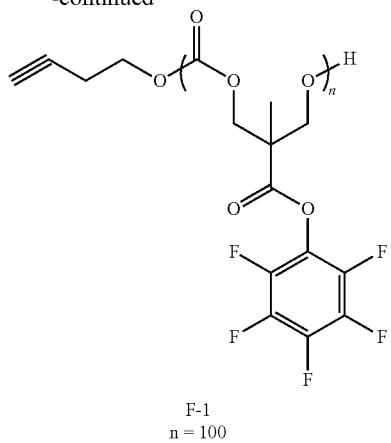

F-1
n = 100

In a nitrogen-purged glovebox, a glass vial was charged with initiator 3-butyn-1-ol (3 mg, 0.01 mmol), MTC-OC6F5 (0.357 g, 1.09 mmol), and 1.45 g of dichloromethane (DCM, 1.0 M with respect to initial concentration of MTC-OC6F5). The MTC-OC6F5 is only partially soluble at this concentration. Trifluoromethanesulfonic acid (triflic acid) (0.008 g, 0.05 mmol) was added to the stirred mixture. As the reaction proceeded, the undissolved MTC-OC6F5 slowly went into solution. The reaction was monitored by $^1$H NMR. Once the reaction was complete (about 12 hours at this catalyst loading and degree of polymerization), polymer F-1 was precipitated into hexanes, isolated, and dried to obtain a white solid (yield: 0.356 g, 99%). $^1$H NMR (CDCl$_3$, 400 MHz): delta=4.48 (s, CH$_2$, 4H), 1.51 (s, CH$_3$, 3H). GPC (RI): Mn (PDI)=22.0 kDa (1.19).

Example 2

Preparation of F-2 (DP=50)

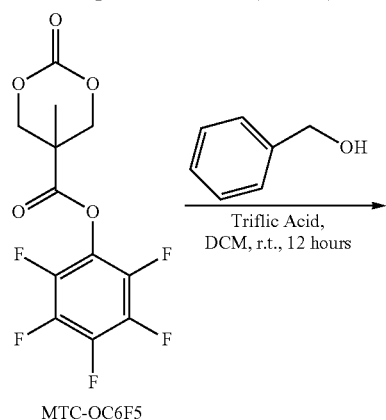

MTC-OC6F5

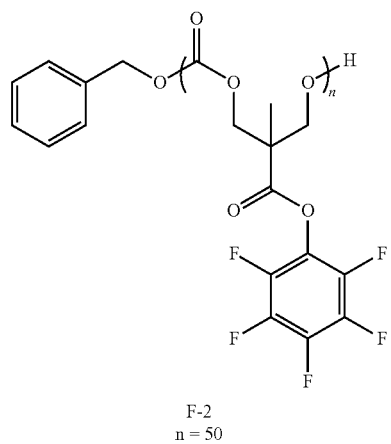

F-2
n = 50

Polymer F-2 (DP=50) was prepared by the procedure of Example 1 using benzyl alcohol as the initiator (2.2 mg, 0.020 mmol), MTC-OC6F5 (0.357 g, 1.09 mmol), 1.45 g of dichloromethane (1.0 M with respect to initial concentration of MTC-OC6F5), and triflic acid (0.008 g, 0.05 mmol). Polymer F-2 was precipitated into hexanes, isolated, and dried to obtain a white solid (yield: 0.356 g, 99%). $^1$H NMR (CDCl$_3$, 400 MHz): delta=4.48 (s, CH$_2$, 4H), 1.51 (s, CH$_3$, 3H). GPC (RI): Mn (PDI)=13.2 kDa (1.21).

Example 3

Preparation of F-3 (DP=32)

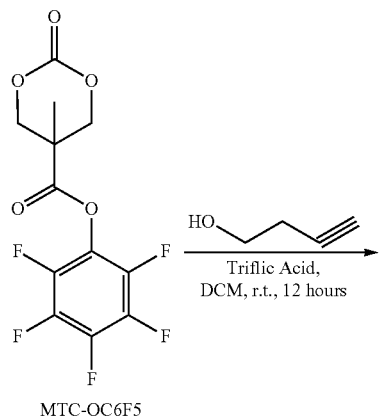

Polymer F-3 (DP=32) was prepared by the procedure of Example 1 using initiator 3-butyn-1-ol (9.9 mg, 0.033 mmol), MTC-OC6F5 (0.357 g, 1.09 mmol), 1.45 g of dichloromethane (1.0 M with respect to initial concentration of MTC-OC6F5) and triflic acid (0.008 g, 0.05 mmol). Polymer F-3 was precipitated into hexanes, isolated, and dried to obtain a white solid (yield: 0.356 g, 99%). $^1$H NMR (CDCl$_3$, 400 MHz): delta=4.48 (s, CH$_2$, 4H), 1.51 (s, CH$_3$, 3H). GPC (RI): Mn (PDI)=7.5 kDa (1.27). DP=32 (by $^1$H NMR endgroup integration/analysis); Mn (by NMR)=10.4 kDa.

Example 4

Preparation of Block Copolymer F-4 (Polycarbonate DP=11)

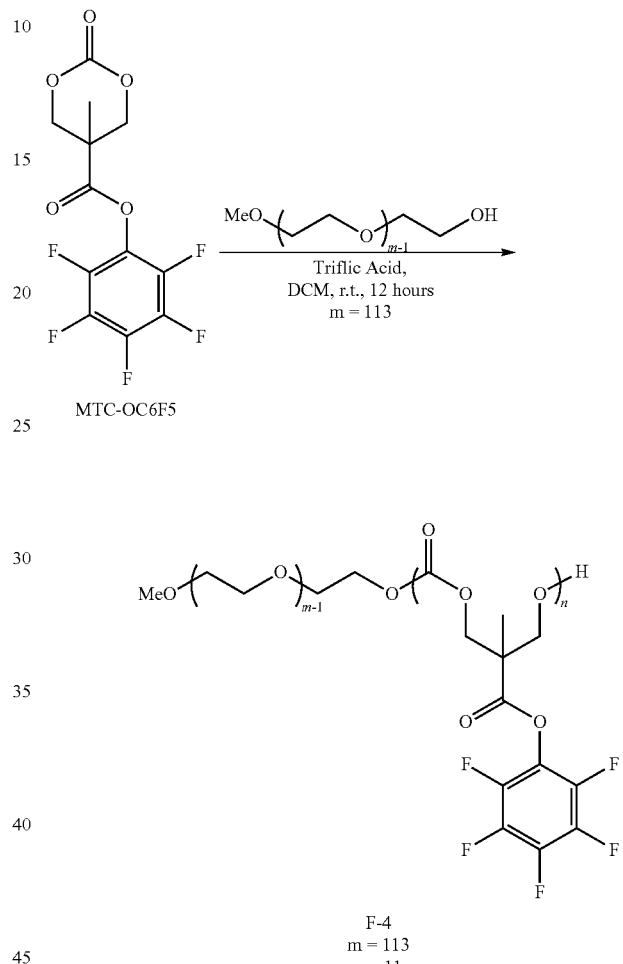

In a nitrogen-purged glovebox, a small vial was charged with 5 kDa mPEG-OH (4.0 g, 0.80 mmol), MTC-OC6F5 (3.39 g, 10.4 mmol), and 10.4 mL of dichloromethane (1 M with respect to MTC-OC6F5). The solution was stirred until the 5 kDa mPEG-OH was fully dissolved. The MTC-OC6F5 is only partially soluble at this concentration. Triflic acid (0.12 g, 0.80 mmol) was added to the stirred solution. As the reaction proceeded, the remaining MTC-OC6F5 slowly dissolved, giving a homogeneous solution. The reaction was monitored by $^1$H NMR. At the end of the reaction, the polymer was precipitated into cold diethyl ether, isolated, and dried to obtain a white solid F-4 (yield: 0.616 g, 62%). $^1$H NMR (CDCl$_3$, 400 MHz): delta=4.46 (s, 4H, carbonate CH$_2$), 3.64 (s, 4H, OCH$_2$CH$_2$), 1.51 (s, 3H, CH$_3$). GPC (RI). Mn (PDI)=11.26 kDa (1.10). DP of MTC-OC6F5 block by NMR=11.

Example 5

Preparation of Block Copolymer F-5

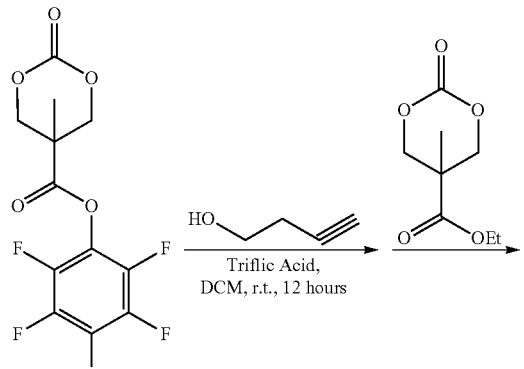

MTC-OC6F5

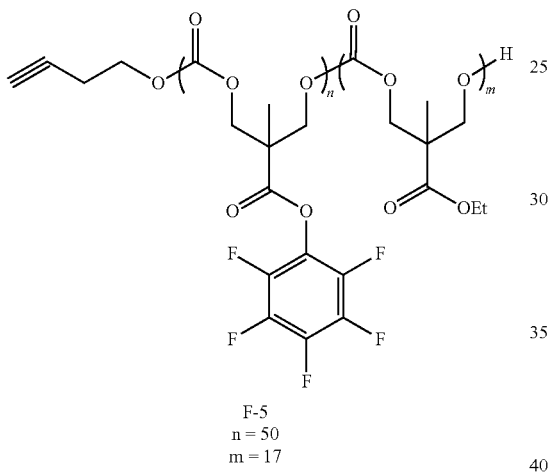

F-5
n = 50
m = 17

In a nitrogen-purged glovebox, a 4-mL glass vial was charged with 3-butyn-1-ol (0.006 g, 0.02 mmol), MTC-OC6F5 (0.357 g, 1.09 mmol), and 1.45 g of dichloromethane (1.0 M with respect to MTC-OC6F5). The solution was stirred until the 3-butyn-1-ol was fully dissolved. The MTC-OC6F5 only partially dissolves at this concentration. Triflic acid (0.008 g, 0.06 mmol) was added to the stirring solution. As the reaction proceeded, the undissolved MTC-OC6F5 slowly went into solution. The reaction was monitored by $^1$H NMR. Once >95% conversion of MTC-OC6F5 was observed, MTC-OEt (0.205 g, 1.09 mmol) was dissolved in minimal dichloromethane and added to the polymerization mixture. Once the conversion of MTC-OEt was greater than 90%, the polymer F-5 was precipitated into hexanes, isolated, and dried to obtain a white solid (yield: 0.476 g, 85%). $^1$H NMR (CDCl$_3$, 400 MHz): delta=4.48 (s, CH$_2$ poly (MTC-OC6F5), 4H), 4.26 (m, CH$_2$ poly(MTC-OEt), 4H), 4.20 (m, CH$_2$CH$_3$ poly(MTC-OEt), 2H), 1.51 (s, CH$_3$, 3H) poly(MTC-OC6F5), 1.26 (m, CH$_3$ poly(MTC-OEt), 3H), 1.26 (m, CH$_2$CH$_3$ poly(MTC-OEt), 3H). GPC (RI): block 1 Mn (PDI)=8770 Da (1.20); blocks 1 and 2 Mn (PDI)=12.5 kDa (1.24).

Formation of N-Heterocycle-Containing Polymers

These amine-functionalized polymers have a name beginning with "A".

Example 6

Preparation of Polymer A-1 (DP=100)

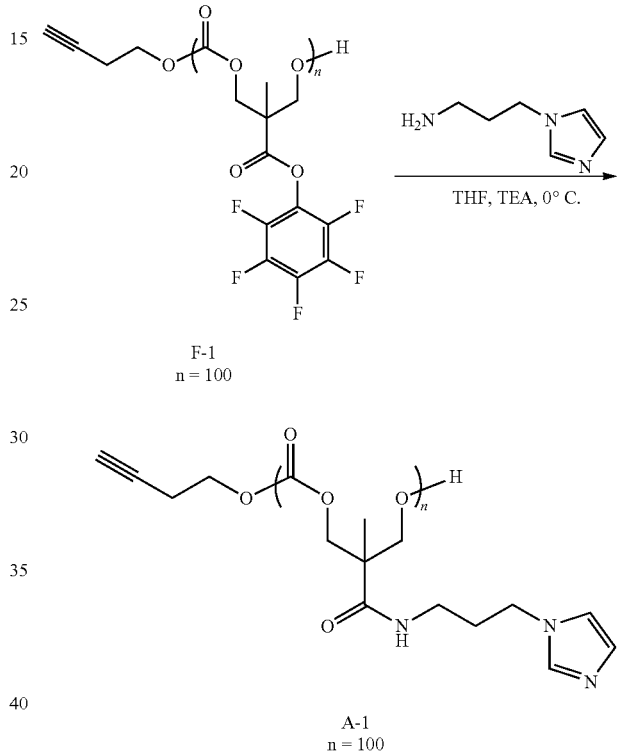

F-1
n = 100

A-1
n = 100

A 20-mL glass vial containing a magnetic stir-bar was charged with F-1 (DP=100, 0.800 g, 2.46 mmol repeat units), anhydrous THF (5.0 mL) and triethylamine (TEA, 0.273 g, 2.70 mmol), and the solution was cooled to 0° C. in an ice-water bath. A solution of 1-(3-aminopropyl)imidazole (APIm, 0.307 g, 2.46 mmol) in THF (1 mL) was added dropwise with vigorous stirring. Turbidity was observed within minutes, followed by the gradual formation of an off-white precipitate. The ice bath was removed and the mixture was allowed to stir for an additional 30 minutes, after which excess diethyl ether (15 mL) was added. The mixture was briefly sonicated and then centrifuged. The mother liquor was decanted and more diethyl ether (20 mL) was added. A second round of sonication, centrifuging, and decanting afforded a white solid A-1 which was then dried under high vacuum for 24 hours. Yield: 0.57 g (87%). $^1$H NMR (MeOD, 400 MHz): delta=7.68 (s, 1H), 7.14 (s, 1H), 6.97 (s, 1H), 4.25 (s, 4H, carbonate CH$_2$), 4.00 (m, 2H), 3.15 (m, 2H), 1.95 (m, 2H), 1.20 (s, 3H, CH$_3$).

Example 7

Preparation of Polymer A-2 (DP=50)

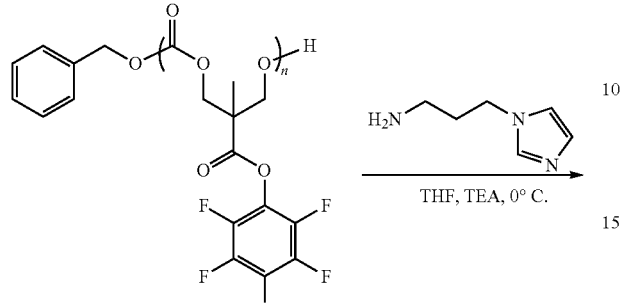

F-2
n = 50

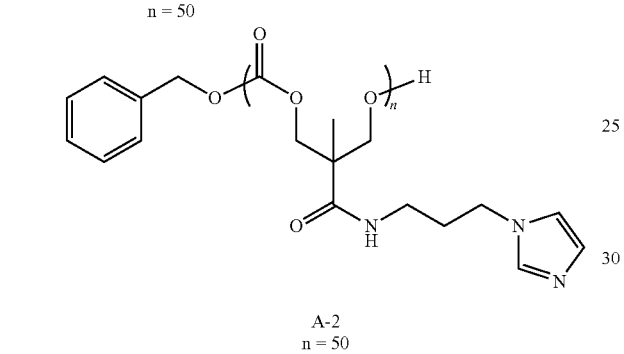

A-2
n = 50

Polymer A-2 (DP=50) was prepared by the procedure of Example 4 using F-2 (0.20 g, 0.613 mmol repeat units), anhydrous THF (1.0 mL), TEA (0.0680 g, 0.674 mmol), and 1-(3-aminopropyl)imidazole (0.0730 g, 0.583 mmol) in THF (0.5 mL), and precipitating A-2 with diethyl ether. Yield: 0.164 g (~100%). $^1$H NMR (MeOD, 400 MHz): delta=7.68 (s, 1H), 7.14 (s, 1H), 6.97 (s, 1H), 4.25 (s, 4H, carbonate CH$_2$), 4.00 (m, 2H), 3.15 (m, 2H), 1.95 (m, 2H), 1.20 (s, 3H, CH$_3$).

Example 8

Preparation of Polymer A-3 (DP=32)

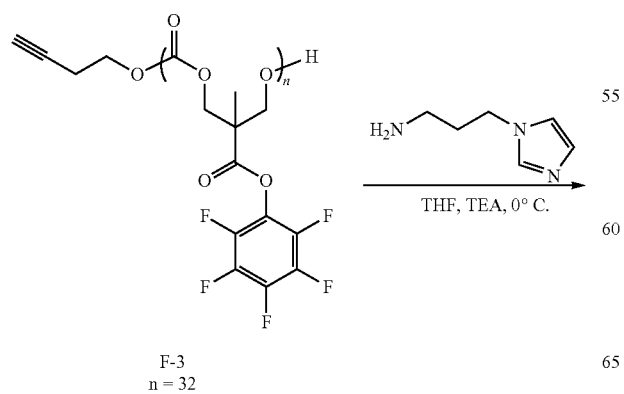

F-3
n = 32

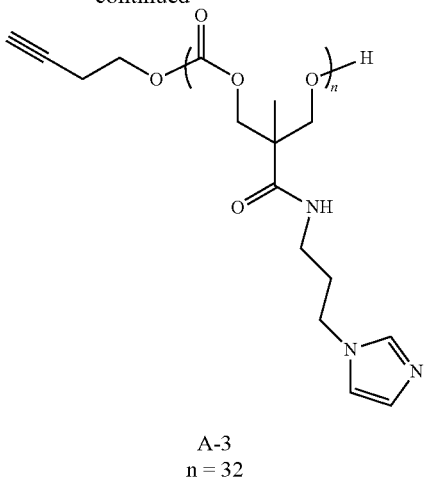

A-3
n = 32

Polymer A-3 (DP=32), was prepared by the procedure of Example 4 using F-3 (DP=32, 0.910 g, 2.79 mmol repeat units), anhydrous THF (5.0 mL), triethylamine (0.31 g, 3.07 mmol), and 1-(3-aminopropyl)imidazole (0.332 g, 2.65 mmol) in THF (1 mL), and precipitating A-3 with diethyl ether. Yield: 0.746 g (~100%). $^1$H NMR (MeOD, 400 MHz): delta=7.68 (s, 1H), 7.14 (s, 1H), 6.97 (s, 1H), 4.25 (s, 4H, carbonate CH$_2$), 4.00 (m, 2H), 3.15 (m, 2H), 1.95 (m, 2H), 1.20 (s, 3H, CH$_3$).

Example 9

Preparation of Polymer A-4 (DP=32)

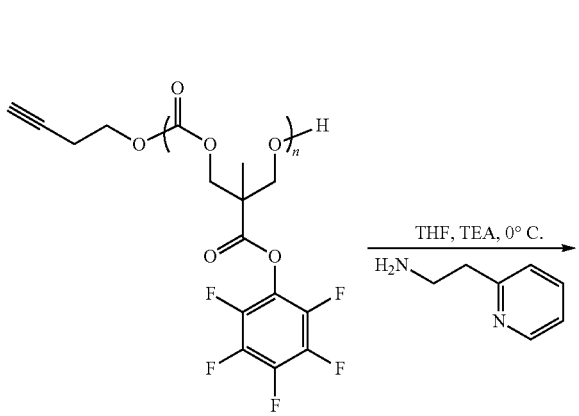

F-3
n = 32

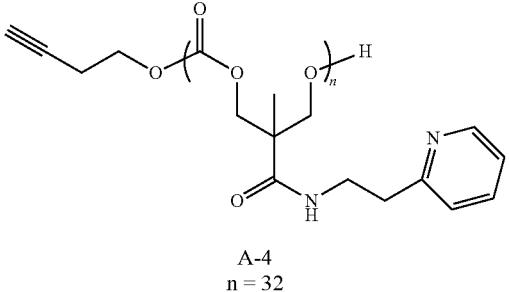

A-4
n = 32

Polymer A-4 (DP=32), was prepared by the procedure of Example 4 using F-3 (0.910 g, 2.79 mmol repeat units), anhydrous THF (5.0 mL), triethylamine (0.311 g, 3.07 mmol), 2-(2'-aminoethyl)pyridine (0.341 g, 2.79 mmol) in THF (1.0 mL), and precipitating A-4 with diethyl ether. Yield: 0.729 g (~99%). ¹H NMR (CDCl₃, 400 MHz): delta=8.45 (pyridine CH, 1H), 7.60 (pyridine CH, 1H), 7.43 (broad s, NH, 1H), 7.14 (pyridine CH, 1H), 7.12 (pyridine CH, 1H), 4.20 (s, carbonate CH₂, 4H), 3.58 (CH₂, 2H), 2.92 (CH₂, 2H), 1.17 (s, CH₃, 3H).

Example 10

Preparation of Polymer A-5 (DP=100)

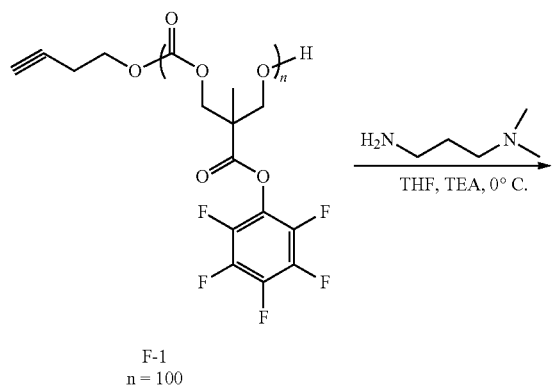

F-1
n = 100

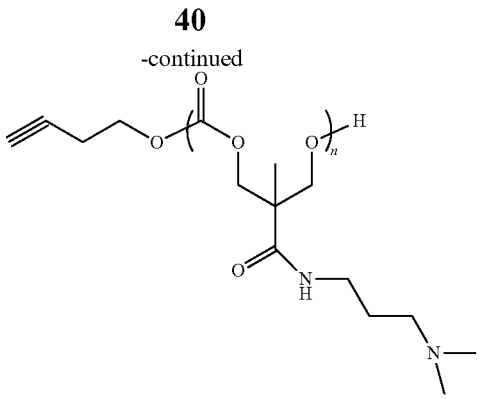

A-5
n = 100

Polymer A-5 (DP=100), was prepared by the procedure of Example 4 using F-1 (0.530 g, 1.62 mmol repeat units), anhydrous THF (3.0 mL), triethylamine (0.200 g, 0.198 mmol), 3-(N,N-dimethylamino)-1-propylamine (0.183 g, 1.79 mmol) in THF (1.0 mL), and precipitating A-5 with diethyl ether. Yield: 0.334 g (84%). ¹H NMR (MeOD, 400 MHz): delta=4.28 (s, carbonate CH₂, 4H), 3.25 (t, CH₂, 2H), 2.55 (CH₂, 2H), 2.41 (—N(CH₃)₂, 6H), 1.75 (CH₂, m, 2H), 1.26 (s, CH₃, 3H). Polymer A-5 is not soluble in water. ¹H NMR was performed in MeOD, and minor degradation was apparent after 1 hour (the time of preparing the sample and acquiring the spectrum). In general, with the dimethylamino moiety, backbone degradation tended to occur in the presence of a nucleophilic solvent such as water or alcohol.

Example 11

Preparation of Polymer A-6 (Polycarbonate DP=10)

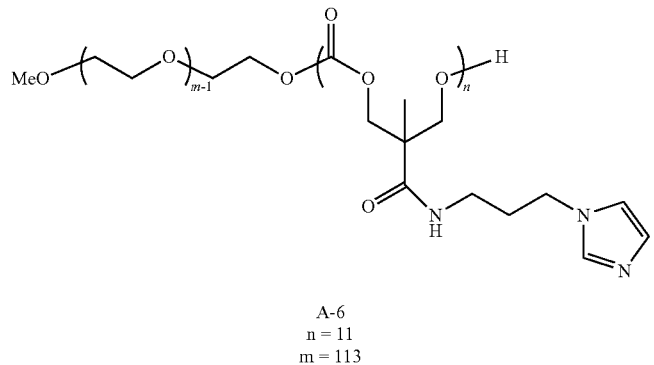

A-6
n = 11
m = 113

A 20-mL glass vial containing a magnetic stir-bar was charged with F-4 (0.60 g, 0.78 mmol repeat units), anhydrous DMF (2.0 mL) and triethylamine (0.079 g, 0.78 mmol). A solution of 1-(3-aminopropyl)imidazole (0.10 g, 0.78 mmol) in DMF (0.5 mL) was added dropwise with stirring. The mixture was allowed to stir for 30 minutes at room temperature, after which it was pipetted into excess diethyl ether (15 mL) to precipitate the polymer. The mixture was briefly sonicated and then centrifuged. The mother liquor was decanted and more diethyl ether (20 mL) was added. A second round of sonication, centrifuging, and decanting afforded a white solid which was then dried under high vacuum for 24 hours. Further purification was carried out using dialysis ($H_2O$) to produce A-6. $^1$H NMR (MeOD, 400 MHz): delta=7.69 (s, 1H), 7.14 (s, 1H), 6.97 (s, 1H), 4.25 (s, 4H, carbonate $CH_2$), 4.01 (m, 2H), 3.64 (s, 4H, $OCH_2CH_2$), 3.14 (m, 2H), 1.96 (m, 2H), 1.20 (s, 3H, $CH_3$).

Example 12

Preparation of Polymer A-7 (Polycarbonate DP=10)

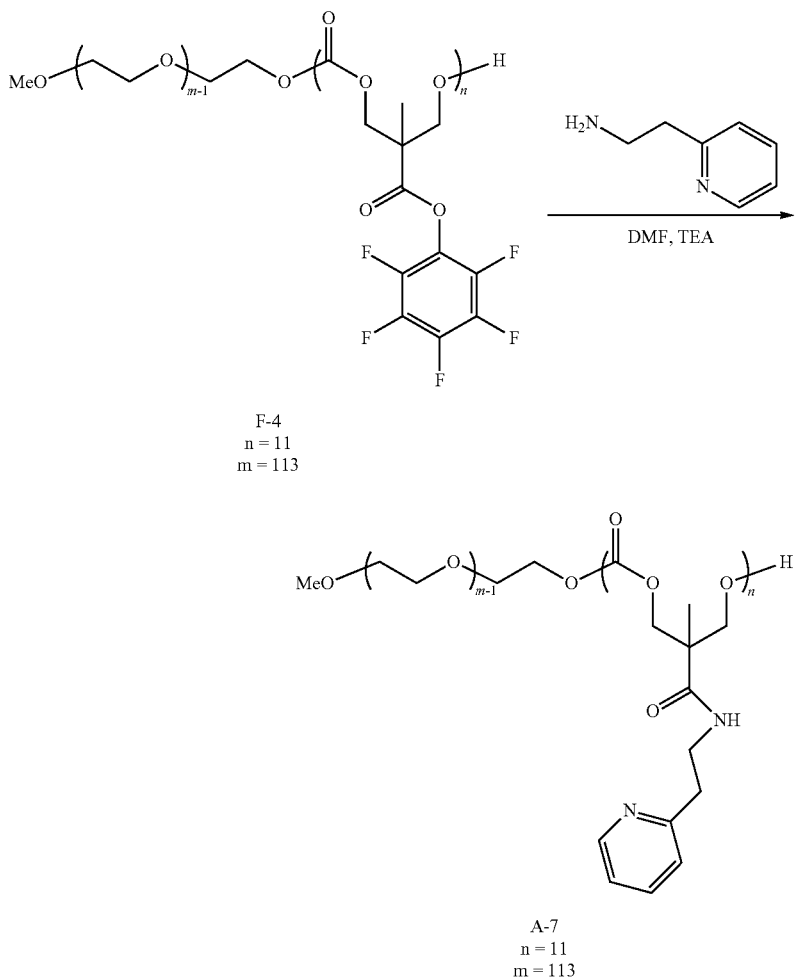

Polymer A-7 was prepared by the procedure of Example 11 using F-4 (0.30 g, 0.39 mmol repeat units), anhydrous DMF (2.0 mL) and triethylamine (0.039 g, 0.39 mmol), 2-(2-aminoethyl)pyridine (0.047 g, 0.39 mmol) in DMF (0.5 mL), and precipitating the polymer in diethyl ether. Further purification was carried out using dialysis ($H_2O$). $^1$H NMR (MeOD, 400 MHz): delta=8.44 (br, 1H), 7.74 (m, 1H), 7.28 (br, 2H), 4.24 (s, 4H, carbonate $CH_2$), 3.65 (s, 4H, $OCH_2CH_2$), 3.50 (m, 2H), 2.95 (m, 2H), 1.19 (s, 3H, $CH_3$).

Example 13

Preparation of Polymer A-8 (Polycarbonate DP=10)

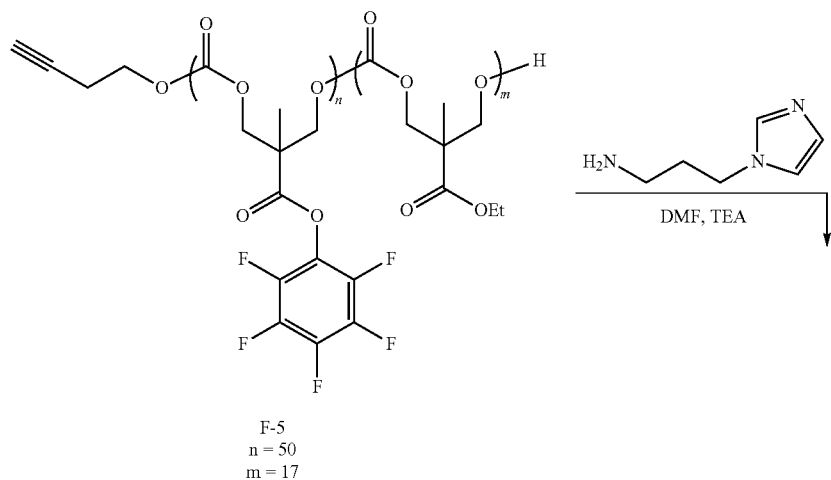

F-5
n = 50
m = 17

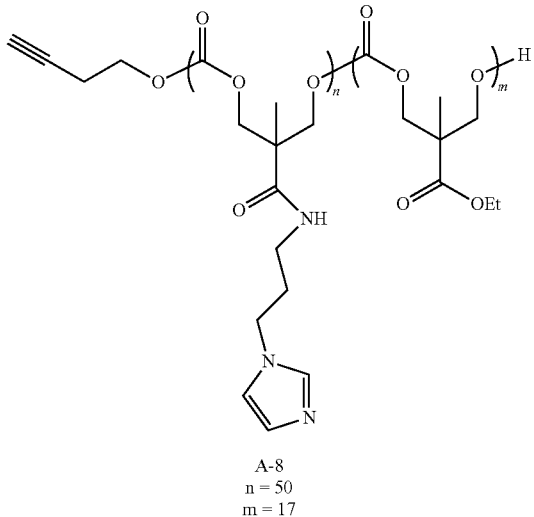

A-8
n = 50
m = 17

A 20-mL glass vial containing a magnetic stir-bar was charged with F-5 (0.700 g, 1.79 mmol of MTC-OC6F5 repeat units), anhydrous THF (5.0 mL) and triethylamine (0.200 g, 1.97 mmol), and the solution was cooled to 0° C. in an ice-water bath. Next, a solution of 1-(3-aminopropyl)imidazole (0.225 g, 1.79 mmol) in THF (1.0 mL) was added dropwise with stirring. The ice-bath was removed and the mixture was allowed to stir for 45 minutes, after which it was pipetted into excess diethyl ether (15 mL) to precipitate the polymer. The mixture was briefly sonicated and then centrifuged. The mother liquor was decanted and more diethyl ether (20 mL) was added. A second round of sonication, centrifuging, and decanting afforded a white solid A-8 which was then dried under high vacuum for 24 hours. $^1$H NMR (MeOD, 400 MHz): delta=7.68 (s, 1H), 7.14 (s, 1H), 6.97 (s, 1H), 4.25 (s, 4H, carbonate CH$_2$), 4.17 (br, 2H), 4.00 (m, 2H), 3.14 (m, 2H), 1.94 (m, 2H), 1.20 (s, 3H, CH$_3$).

Example 14

Preparation of Block Polymer A-9 (Polycarbonate DP=10)

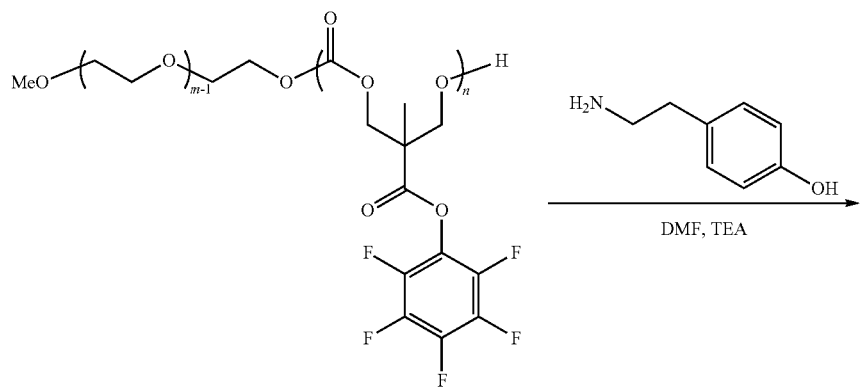

F-4
n = 11
m = 113

A-9
n = 11
m = 113

A 20-mL glass vial containing a magnetic stir-bar was charged with F-4 (0.60 g, 0.77 mmol repeat units), anhydrous DMF (2.0 mL), and tyramine (0.127 g, 0.930 mmol). Next, triethylamine (0.094 g, 0.93 mmol) in DMF (0.5 mL) was added. The reaction mixture was stirred at room temperature (18-20° C.) for 4 hours, after which A-9 was precipitated into diethyl ether. The crude polymer was further purified by dialysis in water.

Example 15

Preparation of Block Polymer A-10 (Polycarbonate DP=11)

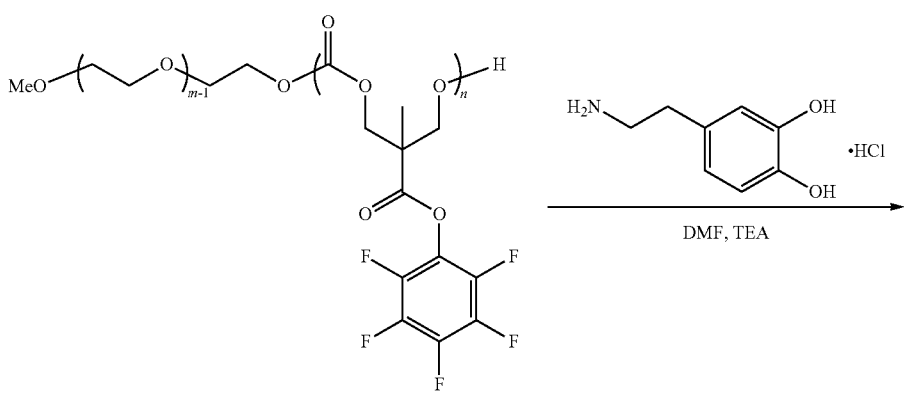

F-4
n = 11
m = 113

-continued

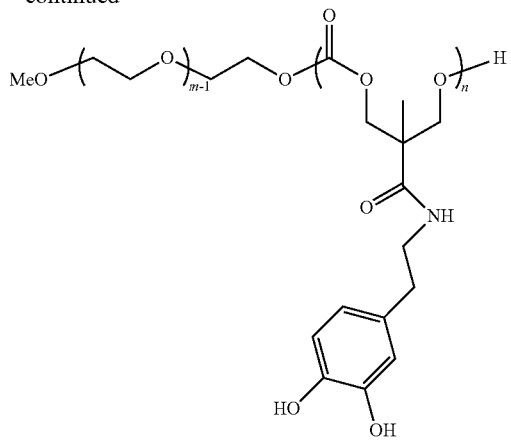

A-10
n = 11
m = 113

A 20-mL glass vial containing a magnetic stir-bar was charged with F-4 (0.60 g, 0.77 mmol repeat units), anhydrous DMF (1.0 mL), and dopamine hydrochloride (0.176 g, 0.930 mmol). Next, triethylamine (0.156 g, 1.55 mmol) was added. The reaction mixture was stirred at room temperature (about 20° C.) for 4 hours, after which A-10 was precipitated into diethyl ether. The crude polymer A-10 was further purified by dialysis in water.

Formation of Poly(Sulfobetaine) Polymers

The zwitterionic sulfobetaine polymers have a name beginning with "S".

Example 16

Preparation of Sulfobetaine Homopolymer S-1
(DP=100)

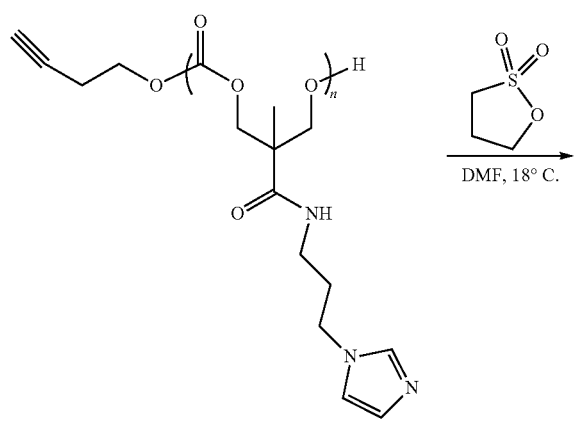

A-1
n = 100

-continued

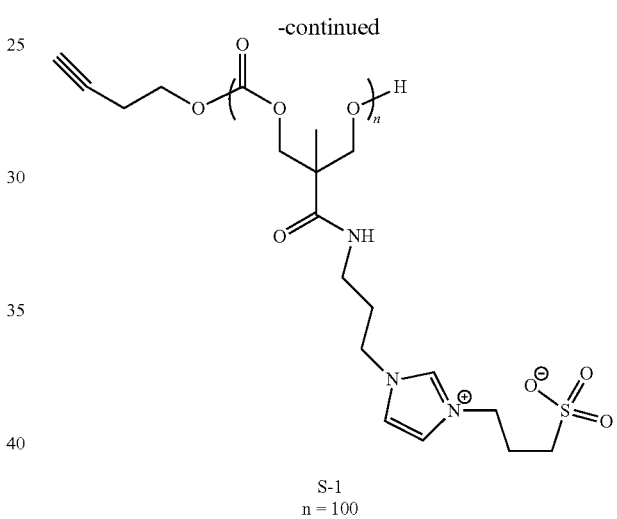

S-1
n = 100

A 20-mL glass vial containing a magnetic stir-bar was charged with A-1 (0.650 g, 2.43 mmol repeat units), 1,3-propanesultone (0.446 g, 3.65 mmol, 1.5 equivalents), and anhydrous DMF (2.0 mL). The reaction mixture was stirred at 18° C. for 24 hours, during which gelation occurred. The gel was dissolved by addition of a minimal volume of water (~0.5 mL), and the resulting solution was precipitated into stirred diethyl ether. The suspension was then centrifuged and the solvent decanted to give the target sulfobetaine polymer S-1 as a white solid. Polymer S-1 was washed with additional portions of ether, dried under high vacuum for 24 hours. $^1$H NMR (D$_2$O, 400 MHz): delta=8.80 (s, 1H, imid), 7.55 (s, 1H, imid), 7.50 (s, 1H, imid), 4.34 (t, 2H, CONH—CH$_2$), 4.24 (broad s, 4H, carbonate), 4.17 (t, 2H), 3.18 (m, 2H), 2.86 (t, 2H), 2.26 (m, 2H), 2.06 (m, 2H), 1.19 (s, 3H, CH$_3$).

Example 17

Preparation of Sulfobetaine Homopolymer S-2 (DP=50)

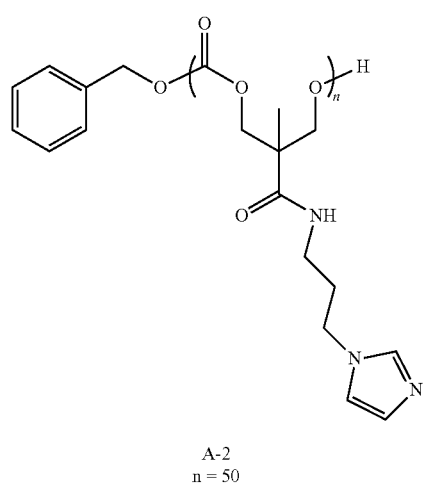

A-2
n = 50

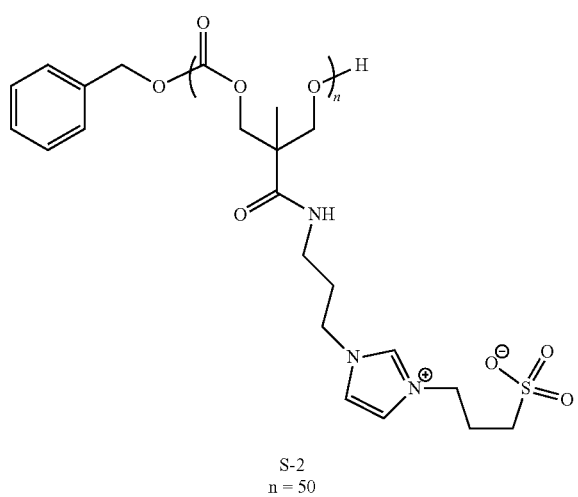

S-2
n = 50

Polymer S-2 (DP=50) was prepared by the procedure of Example 8 using polymer A-2 (0.164 g, 0.613 mmol repeat units), 1,3-propanesultone (0.112 g, 0.920 mmol, 1.5 equivalents), and anhydrous DMF (1.0 mL), and precipitating S-2 with diethyl ether. Yield of white solid: 0.223 g (93%). $^1$H NMR (D$_2$O, 400 MHz): delta=8.80 (s, 1H, N=CH—N), 7.55 (s, 1H, imid), 7.50 (s, 1H, imid), 4.34 (t, 2H, CONH—CH$_2$), 4.24 (broad s, 4H, carbonate), 4.17 (t, 2H), 3.18 (m, 2H), 2.86 (t, 2H), 2.26 (m, 2H), 2.06 (m, 2H), 1.19 (s, 3H, CH$_3$).

Example 18

Preparation of Sulfobetaine Diblock Copolymer S-3

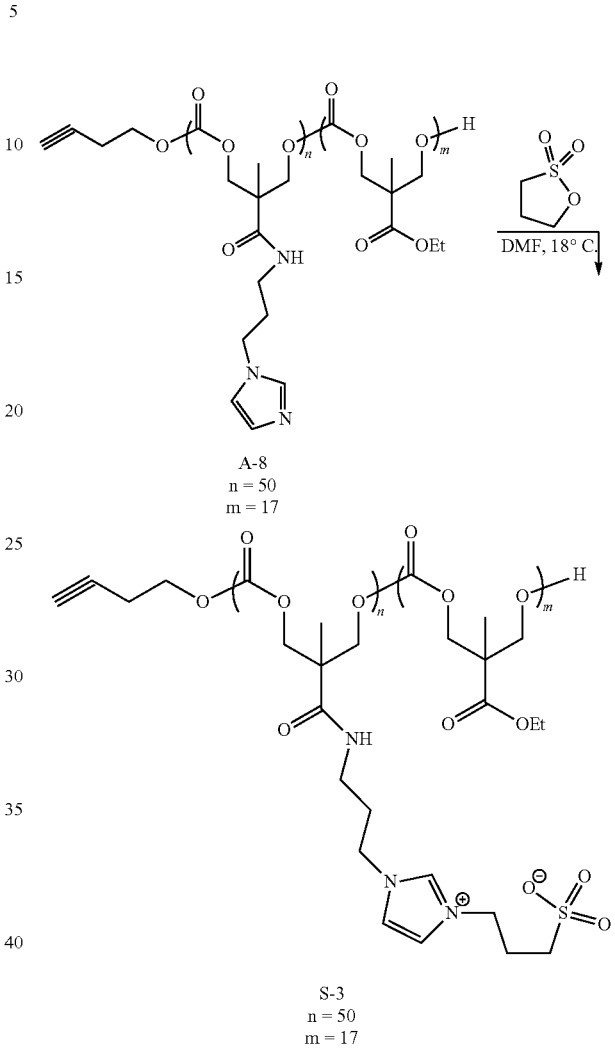

A-8
n = 50
m = 17

S-3
n = 50
m = 17

A 20-mL glass vial containing a magnetic stir-bar was charged with A-8 (0.530 g, 1.60 mmol repeat units), 1,3-propanesultone (0.293 g, 2.40 mmol, 1.5 equivalents), and anhydrous DMF (1.5 mL). The reaction mixture was stirred at room temperature (18° C.) for 24 hours before it was precipitated into stirred diethyl ether. The suspension was then centrifuged and the solvent was decanted to afford the target polymer as a white solid. The polymer S-3 was washed with additional portions of ether, dried under high vacuum for 24 hours. $^1$H NMR (D$_2$O, 400 MHz): delta=8.80 (s, 1H, N=CH—N), 7.55 (s, 1H, imid), 7.50 (s, 1H, imid), 4.34 (t, 2H, CONH—CH$_2$), 4.24 (m, 4H, carbonate), 4.16 (m, 2H), 3.18 (m, 2H), 2.86 (m, 2H), 2.27 (m, 2H), 2.06 (m, 2H), 1.19 (s, 3H, CH$_3$).

Quaternization of N-Heterocyclic Polymers

The quaternized polymers have a name beginning with "Q"

Example 19

Preparation of Quaternary Homopolymer Q-1 (DP=32)

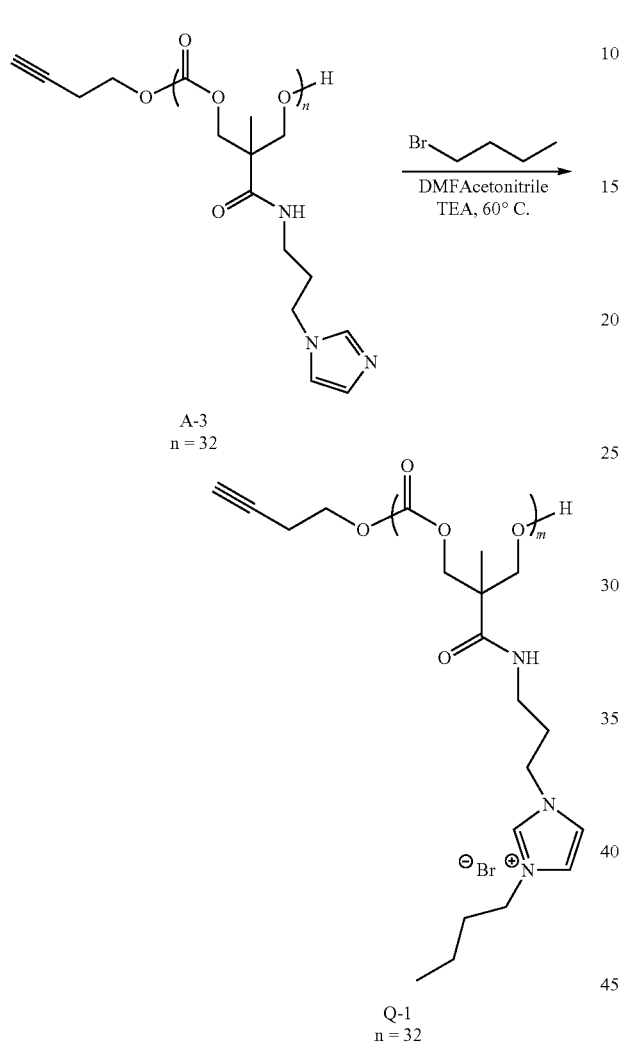

A 20-mL glass vial containing a magnetic stir-bar was charged with A-3 (0.746 g, 2.79 mmol repeat units), 1-bromobutane (0.573 g, 4.18 mmol, 1.5 equivalents), and anhydrous DMF/acetonitrile (2:1 v/v, 6.0 mL). The reaction mixture was heated overnight at 60° C. in the sealed vial, after which it was concentrated under reduced pressure and then precipitated into diethyl ether. The suspension was centrifuged and the mother liquor was decanted off, leaving a white solid which was dried under high vacuum for 24 hours. The solid Q-1 was taken up in deionized water, further purified by dialysis, and then isolated following lyophilization. Yield: 1.01 g (94%). $^1$H NMR (D$_2$O, 400 MHz): delta=8.75 (s, 1H), 7.49 (s, 1H), 7.47 (s, 1H), 4.10-4.30 (br, 8H), 3.17 (m, 2H), 2.05 (m, 2H), 1.79 (m, 2H), 1.25 (m, 2H), 1.19 (s, 3H, CH$_3$), 0.85 (s, 3H, CH$_3$).

Example 20

Preparation of Random Quaternary Copolymer Q-2

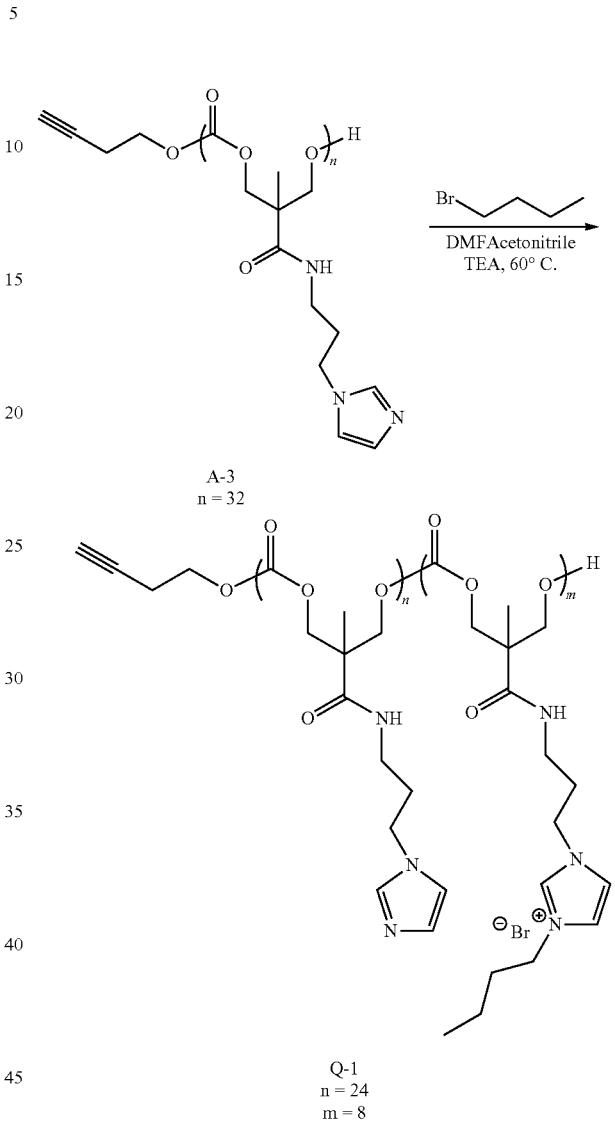

A 20-mL glass vial containing a magnetic stir-bar was charged with A-3 (0.404 g, 1.51 mmol repeat units), 1-bromobutane (0.145 g, 1.06 mmol, 0.7 equivalents), and anhydrous DMF/acetonitrile (2:1 v/v, 4.0 mL). The reaction mixture was heated overnight at 60° C. in the sealed vial, after which it was concentrated under reduced pressure and then precipitated into diethyl ether. The suspension was centrifuged and the mother liquor was decanted off, leaving a white solid which was dried under high vacuum for 24 hours. The polymer Q-2 was further purified by dialysis in deionized water, and then isolated after lyophilization. Yield: 0.483 g (88%). $^1$H NMR (D$_2$O, 400 MHz): delta=8.75 (s, 1H), 7.49 (s, 1H), 7.47 (s, 1H), 4.10-4.30 (br, 8H), 3.17 (m, 2H), 2.05 (m, 2H), 1.79 (m, 2H), 1.25 (m, 2H), 1.19 (s, 3H, CH$_3$), 0.85 (s, 3H, CH$_3$).

Table 6 summarizes the polymer preparations.

TABLE 6

| Example | Name | Structure | DP n | DP m | Mn (kDa) |
|---|---|---|---|---|---|
| 1 | F-1 | F-1  n = 100 | 100 | N/A | 32.6 |
| 2 | F-2 | F-2  n = 50 | 50 | N/A | 16.3 |
| 3 | F-3 | F-3  n = 50 | 32 | N/A | 10.4 |

TABLE 6-continued

| Example | Name | Structure | DP n | DP m | Mn (kDa) |
|---|---|---|---|---|---|
| 4 | F-4 | F-4<br>n = 11<br>m = 113 | 11 | 113 | 8.60 |
| 5 | F-5 | F-5<br>n = 50<br>m = 17 | 50 | 17 | 19.5 |
| 6 | A-1 | | 100 | N/A | 26.7 |
| 7 | A-2 | A-2<br>n = 50 | 50 | N/A | 13.4 |

TABLE 6-continued

| Example | Name | Structure | DP n | DP m | Mn (kDa) |
|---|---|---|---|---|---|
| 8 | A-3 | A-3  n = 32 | 32 | N/A | 8.55 |
| 9 | A-4 | A-4  n = 32 | 32 | N/A | 8.50 |
| 10 | A-5 | A-5  n = 100 | 100 | N/A | 2.44 |
| 11 | A-6 | A-6  n = 11  m = 113 | 11 | 113 | 7.94 |

TABLE 6-continued

| Example | Name | Structure | DP n | DP m | Mn (kDa) |
|---|---|---|---|---|---|
| 12 | A-7 | A-7<br>n = 11<br>m = 113 | 11 | 113 | 7.90 |
| 13 | A-8 | A-8<br>n = 50<br>m = 17 | 50 | 17 | 16.6 |
| 14 | A-9 | A-9<br>n = 11<br>m = 113 | 11 | 113 | 7.93 |

TABLE 6-continued
| Example | Name | Structure | DP n | m | Mn (kDa) |
|---|---|---|---|---|---|
| 15 | A-10 | 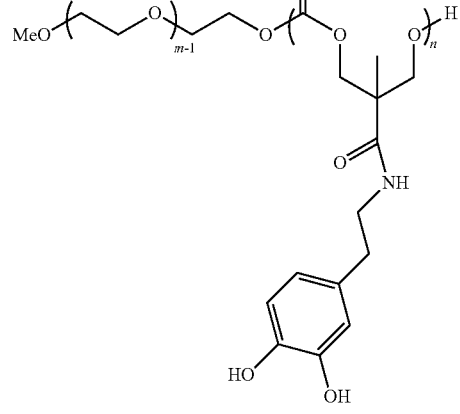<br>A-10<br>n = 11<br>m = 113 | 11 | 113 | 8.25 |
| 16 | S-1 | 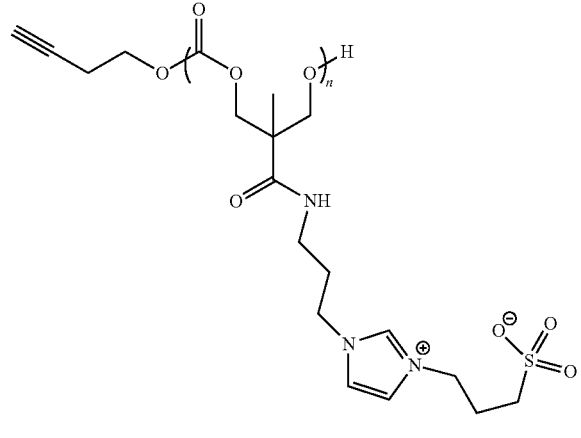<br>S-1<br>n = 100 | 100 | N/A | 3.90 |
| 17 | S-2 | 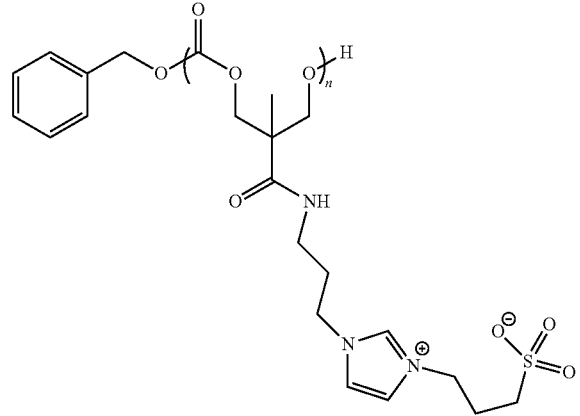<br>S-2<br>n = 50 | 50 | N/A | 19.5 |

TABLE 6-continued
| Example | Name | Structure | DP n | m | Mn (kDa) |
|---|---|---|---|---|---|
| 18 | S-3 | 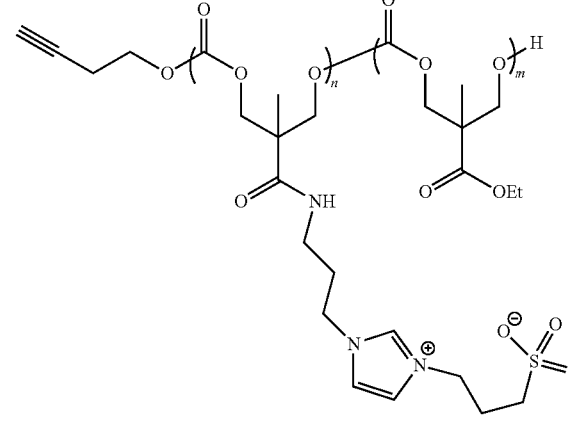 S-3 n = 50 m = 17 | 50 | 17 | 22.7 |
| 19 | Q-1 | 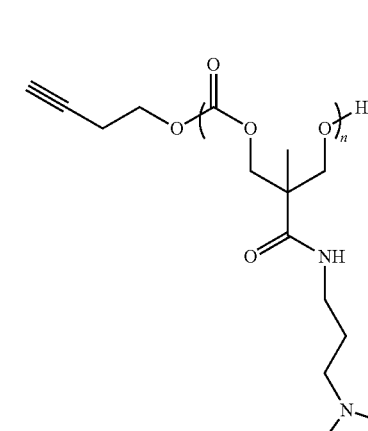 Q-1 m = 32 | N/A | 32 | 40.5 |

TABLE 6-continued

| Example | Name | Structure | DP n | DP m | Mn (kDa) |
|---|---|---|---|---|---|
| 20 | Q-2 | Q-1 n = 24 m = 8 | 24 | 8 | 12.9 |

Cell Viability Test

Two sulfobetaine homopolymers (S-1 and S-2) and one amphiphilic sulfobetaine diblock copolymer (S-3) were chosen as representative polymers for the toxicity tests involving human embryonic kidney (HEK293) cell lines. Poly (ethylene glycol) (PEG) polymers (Mn=5 kDa and 10 kDa) were used as controls.

HEK293 cells were cultured in RPMI-1640 supplied with 10% fetal bovine serum (FBS) and 1% penicillin-streptomycin. HEK293 cells were seeded onto 96-well plates at a density of 10,000 cells/well. The cells were incubated at 37° C., 5% $CO_2$. After 24 hours, the medium was replaced with fresh medium containing a polymer at various concentrations. After being incubated for 48 hours, 100 microliters of fresh medium and 20 microliters of 5 mg/mL (3-(4,5-dimethylthiazol-2-yl)-2,5-diphenyltetrazolium bromide (i.e., MTT) solution were used to replace the sample medium. After 4 hours of incubation, the medium was removed, and DMSO (150 microliters) was added to each well to dissolve the formazan crystals. The absorbance of each well was measured as the absorbance at 550 nm minus the absorbance at 690 nm using a microplate reader (Power-Wave X, Bio-tek Instruments, U.S.A.). The results were presented as a percentage of the absorbance at 550 nm of a blank control.

Similar to both PEG polymers, the three sulfobetaine polycarbonates S-1 to S-3 did not show significant cytotoxicity (FIGS. 1 to 5, bar graphs).

Polymer Aggregation Studies

The stability and aggregation properties of the three sulfobetaine polymers S-1 to S-3 were investigated by measuring particle size change of polymers in a phosphate-buffered saline (PBS) medium containing fetal bovine serum (FBS). Proteins of the serum-containing medium can bind to the synthetic polymer, resulting in aggregation of the micelle particles that is detectable by a change in particle size. The sulfobetaine polymers were dissolved in PBS containing 10% fetal bovine serum (FBS) at pH 7.4. PBS containing 10% FBS was used as a control. The particle sizes of polymer solutions were analyzed using 90Plus/BI-MAS (Brookhaven Instruments Corporation, Holtsville, N.Y.) equipped with a He—Ne laser beam at 658 nm (scattering angle: 90°) over 24 hours or 48 hours. The initial concentration of the sulfobetaine polymers was 500 mg/L. Each sample was measured 3 times and an average particle size was obtained.

Figure 6:
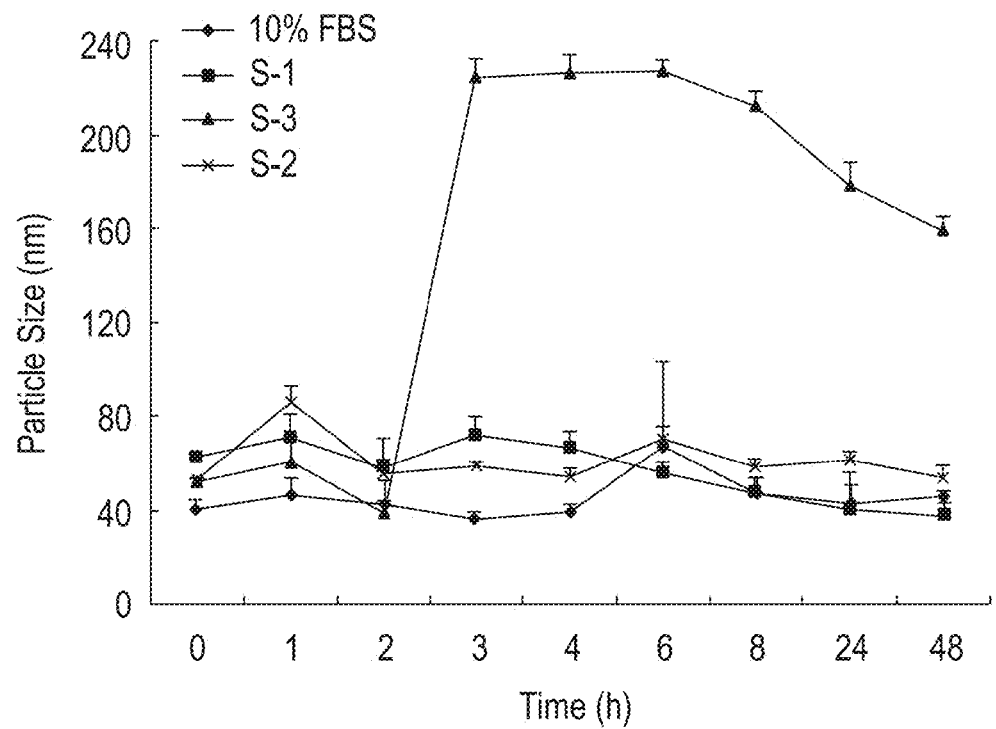
FIG. 6 is a graph showing the particle size growth of S-1, S-2 and S-3 versus incubation time up to 48 hours using phosphate buffered saline (PBS) containing 10% serum. Polymer-protein aggregation was observed with S-3. No polymer-protein aggregation was observed with S-1 and S-2.

Similar to the behavior of PBS containing only FBS, the S-1 and S-2 particle sizes were stable over a period of 48 hours (FIG. 6) in PBS containing 10% FBS, indicating that there was no aggregation of the micelle particles. However, aggregation of S-3 micelles was observed after 2 hours of incubation. Without being bound by theory, the S-3 micelle aggregation may arise from the influence of the hydrophobic block derived from MTC-OEt.

Critical Micelle Concentration (CMC)

The CMC was determined by following the scattering intensity (Dynamic Light Scattering) of the polymer solutions at various polymer concentrations. Mixed micelles of two different polymers were prepared by dissolving equal weights of each polymer together in water. Table 7 lists the CMC, particle size, and PDI of the individual amine polymers A-6, A-7, A-9, and A-10 and the mixed micelles formed with combinations of these polymers.

TABLE 7

| Ex. | Polymer 1 | Polymer 2 | Description | CMC (ppm) |
|---|---|---|---|---|
| 21 | A-9 | | Micelle | 120 |
| 22 | A-10 | | Micelle | 100 |
| 23 | A-6 | | Micelle | 210 |
| 24 | A-7 | | Micelle | 290 |

TABLE 7-continued

| Ex. | Polymer 1 | Polymer 2 | Description | CMC (ppm) |
|---|---|---|---|---|
| 25 | A-9 | A-6 | Mixed Micelle | 190 |
| 26 | A-9 | A-7 | Mixed Micelle | 180 |
| 27 | A-10 | A-6 | Mixed Micelle | 190 |
| 28 | A-10 | A-7 | Mixed Micelle | 170 |

Table 8 lists the particle sizes of the micelles alone (no DOX). Examples 29 to 32 were prepared from an individual polymer. Examples 33 to 36 ("mixture of micelles") were prepared by first dissolving the individual polymers in separate solutions and then mixing the solutions together. Examples 37-40 ("mixed micelle") were prepared by dissolving the two polymers together in solution. Examples 31-33, and 37 were bimodal in particle size distribution.

TABLE 8

| Ex. | Polymer 1 | Polymer 2 | Description | Particle size (nm) | Polydispersity (PDI) |
|---|---|---|---|---|---|
| 29 | A-9 | | Micelle | 28.8 | 0.103 |
| 30 | A-10 | | Micelle | 24.6 | 0.05 |
| 31 | A-6 | | Micelle | 20.1, 163.6 | 0.295 |
| 32 | A-7 | | Micelle | 91.1, 294.1 | 0.390 |
| 33 | A-9 | A-6 | Mixture of Micelles | 27.5, 342.6 | 0.453 |
| 34 | A-9 | A-7 | Mixture of Micelles | 28.3, 567.4 | 0.331 |
| 35 | A-10 | A-6 | Mixture of Micelles | 25.4 | 0.078 |
| 36 | A-10 | A-7 | Mixture of Micelles | 24.2 | 0.08 |
| 37 | A-9 | A-6 | Mixed Micelle | 27.5, 385.8 | 0.453 |
| 38 | A-9 | A-7 | Mixed Micelle | 28.5 | 0.068 |
| 39 | A-10 | A-6 | Mixed Micelle | 25.6 | 0.097 |
| 40 | A-10 | A-7 | Mixed Micelle | 24.1 | 0.073 |

Preparation and Characterization of DOX-Loaded Micelles

Encapsulation of Doxorubicin (DOX) into the above micelles was performed using a sonication/membrane dialysis method. DOX (5 mg) was dissolved in 1.5 mL of dimethylacetamide (DMAc) and neutralized with three moles excess of triethylamine. The polymer solution, in which 10 mg of polymer was dissolved in 0.5 mL of DMAc, was added into the DOX solution and mixed by vortex for 5 minutes. The solution containing drug and polymer was added dropwise to de-ionized (DI) water (10 mL) with sonication for 2 minutes at 130 W using a probe-based sonicator (Vibra Cell VCX 130). The solution was then dialyzed against 1000 mL of DI water for 48 hours using a dialysis bag with molecular weight cut-off of 1000 Da (Spectra/Por 7, Spectrum Laboratories Inc.). The water was changed every 3 hours for the first 6 hours and once again the next day. The DOX-loaded micelles were collected by lyophilization after 2 days. The amount of DOX loaded was measured by dissolving a known amount of DOX-loaded micelles in 1 mL of DMSO and measuring the absorbance using a UV-Vis spectrophotometer (UV 2501PC Shimadzu, Japan) at 480 nm. DOX loading level was calculated based on the following formula: DOX loading level (wt %)=[(mass of DOX found)/(mass of DOX-loaded micelles)]×100%.

Dynamic Light Scattering (DLS) Measurement

The particle size of the freshly prepared DOX-loaded micelles was measured using Zetasizer 3000 HAS (Malvern Instrument Ltd., Malvern, UK) equipped with a He—Ne laser beam at 658 nm (dynamic light scattering, scattering angle: 90°). Each measurement was repeated five times. An average value was obtained from the five measurements. Multimodel analysis was chosen to conduct the size measurements to maximize the resolution as the samples might contain individual micelles and aggregates.

Table 9 lists the feed amounts of each starting material used to make the DOX-loaded micelles.

TABLE 9

| | | | Feed | | |
| Ex. | Polymer 1 | Polymer 2 | Polymer 1 (mg) | Polymer 2 (mg) | DOX (mg) | Description |
|---|---|---|---|---|---|---|
| 41 | A-9 | | 10 | 0 | 5 | Micelle |
| 42 | A-10 | | 10 | 0 | 5 | Micelle |
| 43 | A-6 | | 10 | 0 | 5 | Micelle |
| 44 | A-7 | | 10 | 0 | 5 | Micelle |
| 45 | A-9 | A-6 | 5.05 | 4.95 | 5 | Mixed Micelle |
| 46 | A-9 | A-7 | 5.05 | 4.95 | 5 | Mixed Micelle |
| 47 | A-10 | A-6 | 5.1 | 4.9 | 5 | Mixed Micelle |
| 48 | A-10 | A-7 | 5.1 | 4.9 | 5 | Mixed Micelle |

Figure 7:
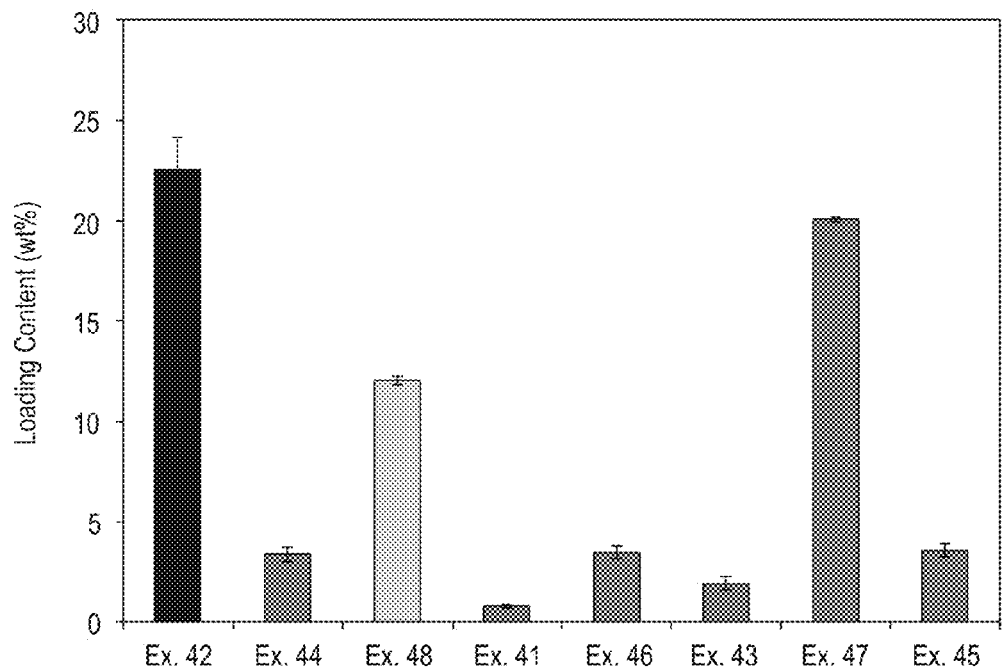
FIG. 7 is a bar chart showing the drug loading content (wt %) of Examples 42 to 48.

Table 10 lists the analyzed weight percent (wt %) of DOX in the DOX-loaded micelles, based on total dry weight of the DOX-loaded micelles. Table 10 also lists the particle sizes and the polydispersity index (PDI) of the DOX-loaded micelles. The DOX loading levels are also duplicated in the bar graph of FIG. 7.

TABLE 10

| Ex. | Polymer 1 | Polymer 2 | Description | Analyzed DOX (wt %) | Particle size (nm) | (PDI) |
|---|---|---|---|---|---|---|
| 41 | A-9 | | Micelle | 0.7 | 793, 105 | 0.510 |
| 42 | A-10 | | Micelle | 22.5 | 47 | 0.206 |
| 43 | A-6 | | Micelle | 1.8 | 315 | 0.327 |
| 44 | A-7 | | Micelle | 3.4 | 187 | 0.139 |
| 45 | A-9 | A-6 | Mixed Micelle | 3.4 | 429 | 0.388 |
| 46 | A-9 | A-7 | Mixed Micelle | 3.4 | 100, 17 | 0.334 |
| 47 | A-10 | A-6 | Mixed Micelle | 19.9 | 533 | 0.311 |
| 48 | A-10 | A-7 | Mixed Micelle | 12.0 | 37 | 0.263 |

In Vitro Release of DOX from Mixed Micelles

The following procedure was used to measure the release of DOX from DOX-loaded mixed micelles of Example 47. DOX-loaded micelles solutions at a concentration of 1 mg/mL (5 mL) were transferred to dialysis membrane tubes with a molecular weight cutoff of 1000 Da. The tubes were then immersed in a beaker containing 50 mL phosphate buffered saline (PBS) at 37° C., pH 7.4. The tubes were shaken at a speed of 100 rev/min. At specific time intervals, 1 mL of the release medium was withdrawn and replaced with 1 mL of fresh PBS. The DOX content in the samples was analyzed using a UV-Vis spectrophotometer at 480 nm.

Figure 8:
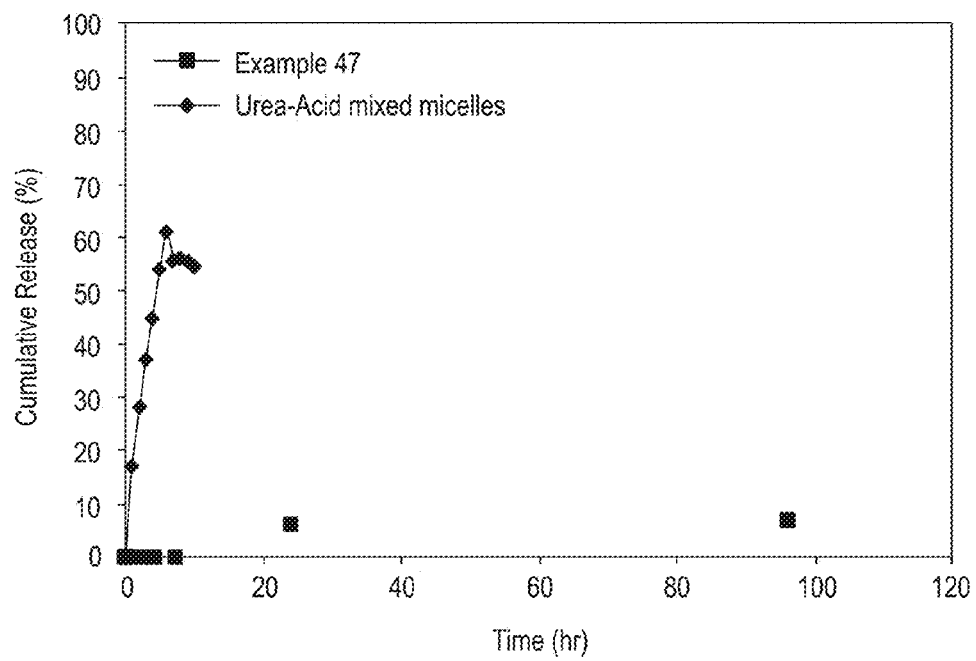
FIG. 8 is a graph comparing the drug release profile for the nanoparticles of Example 47 containing 19 wt % Doxorubicin (DOX) with DOX-loaded urea-acid mixed micelles PEG-PAC/PEG-PUCS1 1:1. Almost no DOX was released in 120 hours from Example 47 nanoparticles whereas the DOX-loaded urea-acid mixed micelles released 60% of the Doxorubicin within about 6 hours.

FIG. 8 shows the drug release profile for Example 47 in the PBS medium. Almost no DOX was released (<about 8%) over a period of 120 hours, indicating the DOX was tightly held by the mixed micelle particles.

For comparison, FIG. 8 includes the release profile of a DOX-loaded acid-urea mixed micelle prepared from two polymers, PEG-PAC and PEG-PUCS1 having the following structures:

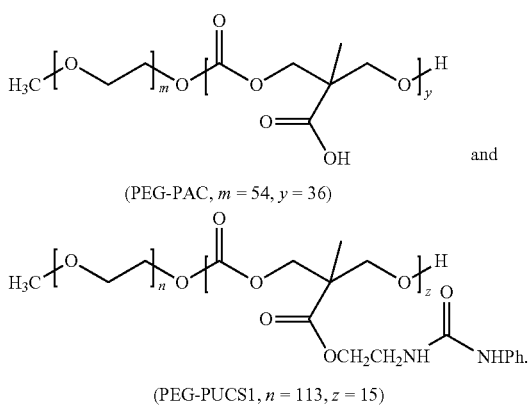

(PEG-PAC, m = 54, y = 36)

(PEG-PUCS1, n = 113, z = 15)

The polymers and DOX-loaded mixed micelles were prepared according to C. Yang, et al., "Supramolecular nanostructures designed for high cargo loading capacity and kinetic stability," Nano Today 2010, 5, pages 515-523. The benzyl ester precursor to PEG-PAC had Mn=11.4 kDa and PDI=1.2. The CMC of PEG-PAC was 152.8 mg/L. The loaded mixed micelle, named PEG-PAC/PEG-PUCS1 1:1, which contained a 1:1 molar ratio of acid:urea groups, had a CMC of 15.8 mg/L. The DOX-loaded mixed micelles of PEG-PAC/PEG-PUCS1 1:1 contained 40 wt % DOX, had an average particle size of 177 nm, and released about 60% of the DOX to the medium within about 6 hours (ibid., FIG. 5a, page 522).

HepG2 Cell Viability of DOX-Loaded Micelles

Figure 9:
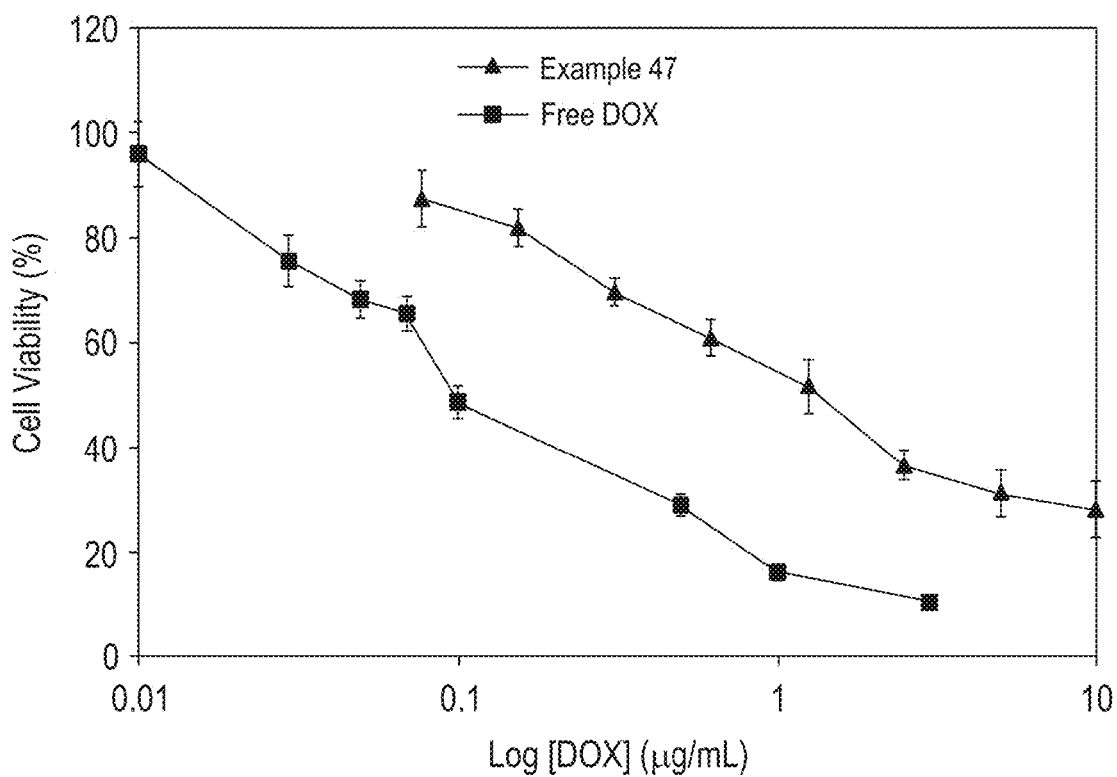
FIG. 9 is a graph comparing the cell viability of HepG2 cells when treated with the DOX-containing nanoparticles of Example 47 and free DOX. The results indicate the Example 47 nanoparticles release the DOX when contacted by HepG2 cells, and kill the HepG2 cells.

The cell viability test procedure described further above was followed using HepG2 liver carcinoma cells. The HepG2 cells were exposed 48 hours to the DOX-loaded mixed micelles of Example 47. Free DOX served as a control. FIG. 9 shows the toxicity profile of the Example 47 DOX-loaded mixed micelles mimics the free DOX profile shifted to higher DOX concentration. The results indicate that the DOX-loaded mixed micelles of Example 47 have higher selectivity for releasing the drug compared to the PEG-PAC/PEG-PUCS1 1:1 DOX-loaded micelles, and the release from the Example 47 DOX-loaded mixed micelles is triggered by contact with the HepG2 cells. The released drug is effective in killing the target HepG2 cells.

Summary

The disclosed biodegradable mixed micelles are effective carriers for a drug. The drug-loaded mixed micelles nanoparticles exhibit several beneficial properties. The nanoparticles can be less prone to aggregate in a serum medium and can retain 90% or more of the drug when exposed to serum medium for a period of 5 days, yet can release the drug when contacted by a target cell. These characteristics are promising for reducing toxic side effects of a given drug at a given dosage without sacrificing drug efficiency. The micelles can be functionalized with a wide variety of functional groups to control particle size, aggregation behavior with respect to serum proteins, drug binding properties, drug release properties, and cell recognition properties. Potential uses include cancer therapies and antibiotic treatments for which the cargo drug is the primary, if not only, therapeutic agent.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A nanoparticle, comprising:
   a drug;
   a first block polymer comprising i) a first poly(ethylene oxide) block (first PEO block) and ii) a first polycarbonate block linked to the first PEO block, wherein a) the first polycarbonate block comprises a first repeat unit comprising an aliphatic carbonate backbone portion and a side chain linked to the backbone portion, b) the side chain of the first repeat unit comprises an aromatic nitrogen-containing heterocycle (N-heterocycle), and c) the N-heterocycle of the side chain of the first repeat unit is present as a base, a hydrosalt of the base, a sulfobetaine adduct of the base, or a combination thereof; and
   a second block polymer comprising i) a second PEO block and ii) a second polycarbonate block linked to the second PEO block, wherein a) the second polycarbonate block comprises a second repeat unit comprising an aliphatic carbonate backbone portion and a side chain linked to the backbone portion and b) the side chain of the second repeat unit comprises a catechol group;
   wherein
   the drug, the first block polymer, and the second block polymer of the nanoparticle are bound at least by non-covalent interactions,
   the nanoparticle is water-dispersible, and
   the nanoparticle is capable of controlled release of the drug in a medical treatment.

2. The nanoparticle of claim 1, wherein the drug is a protein.

3. The nanoparticle of claim 1, wherein the drug is a gene.

4. The nanoparticle of claim 1, wherein the drug is an anthracycline antibiotic.

5. The nanoparticle of claim 1, wherein the drug is Doxorubicin.

6. The nanoparticle of claim 1, wherein the N-heterocycle of the first repeat unit is selected from the group consisting of imidazoles, pyridines, and combinations thereof.

7. The nanoparticle of claim 1, wherein the N-heterocycle of the first repeat unit is an imidazole.

8. The nanoparticle of claim 1, wherein the N-heterocycle of the first repeat unit includes a quaternary nitrogen.

9. The nanoparticle of claim 1, wherein the N-heterocycle of the first repeat unit is present as a sulfobetaine adduct.

10. The nanoparticle of claim 1, wherein the first polycarbonate block is a homopolymer of the first repeat unit.

11. The nanoparticle of claim 1, wherein the second polycarbonate block is a homopolymer of the second repeat unit.

12. The nanoparticle of claim 1, wherein the first PEG block and the second PEG block independently have a degree of polymerization (DP) of about 80 to about 200.

13. The nanoparticle of claim 1, wherein the nanoparticle has an average circular diameter of about 20 nm to about 700 nm.

14. A method, comprising:
forming a first mixture comprising a drug and a water miscible organic solvent;
forming a second mixture by dissolving together in water a first block polymer and a second block polymer;
combining the first mixture and the second mixture, thereby forming a third mixture; and
removing the organic solvent from the third mixture, thereby forming a water dispersible nanoparticle comprising the drug, the first block polymer, and the second block polymer bound at least by non-covalent interactions;
wherein
the first block polymer comprises i) a first poly(ethylene oxide) block (first PEO block) and ii) a first polycarbonate block linked to the first PEO block, wherein the first polycarbonate block comprises a first repeat unit, the first repeat unit comprises an aliphatic carbonate backbone portion and a side chain linked to the backbone portion, the side chain of the first repeat unit comprises an aromatic nitrogen-containing heterocycle (N-heterocycle), and the N-heterocycle has the form of a base, a hydrosalt of the base, a sulfobetaine adduct of the base, or a combination thereof,
the second block polymer comprises i) a second PEO block and ii) a second polycarbonate block linked to the second PEO block, wherein the second polycarbonate block comprises a second repeat unit comprising an aliphatic carbonate backbone portion and a side chain linked to the backbone portion, and the side chain of the second repeat unit comprises a catechol group, and
the nanoparticle is capable of controlled release of the drug in a medical treatment.

15. The method of claim 14, wherein the nanoparticle comprises the drug in an amount of about 1 wt % to about 30 wt % based on total dry weight of the nanoparticles.

16. The method of claim 14, wherein the catechol group of the second block polymer of the nanoparticle is present as a polymerized form of the catechol group.

17. The method of claim 14, wherein the catechol group of the second block polymer of the nanoparticle is present as an oxidized form of the catechol group.

18. A nanoparticle, comprising:
a) a drug;
b) a first block polymer having the formula (1):

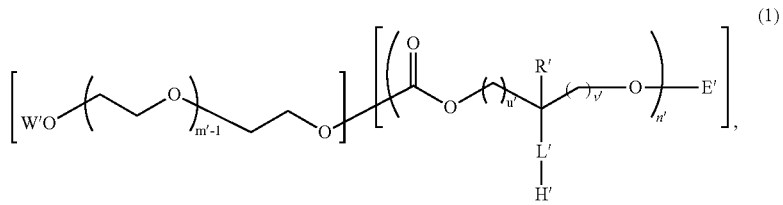

wherein
u' is a positive integer from 0 to 6,
v' is a positive integer from 0 to 6,
u' and v' cannot both be zero,
n' is a positive number of 2 to about 50,
m' is a positive number of about 80 to about 200,
E' is a monovalent end group selected from the group consisting of hydrogen and functional groups comprising 1 or more carbons,
H' is a functional group selected from the group consisting of non-charged aromatic nitrogen-containing heterocycles, hydrosalts of aromatic nitrogen-containing heterocycles, sulfobetaine adducts of aromatic nitrogen-containing heterocycles, and combinations thereof,
L' is a divalent linking group comprising 2 or more carbons,
R' is a monovalent radical selected from the group consisting of hydrogen and alkyl groups comprising 1 to 6 carbons, and
W' is a monovalent end group comprising 1 to 10 carbons; and
c) a second block polymer having the formula (4):

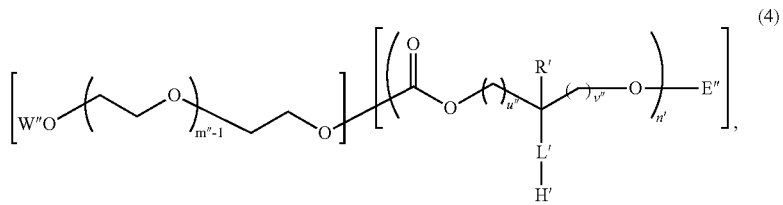

wherein
u" is a positive integer from 0 to 6,
v" is a positive integer from 0 to 6,
u" and v" cannot both be zero,
n" is a positive number of 2 to about 50,
m" is a positive number of about 80 to about 200,
E" is a monovalent end group selected from the group consisting of hydrogen and functional groups comprising 1 or more carbons,
C" is a moiety comprising a catechol group,
L" is a divalent linking group comprising 2 or more carbons,
R" is a monovalent radical selected from the group consisting of hydrogen and alkyl groups comprising 1 to 6 carbons, and
W" is a monovalent end group comprising 1 to 10 carbons;

wherein
components a), b), and c) of the nanoparticle are bound at least by non-covalent interactions,
the nanoparticle is dispersible in water, and
the nanoparticle is capable of controlled release of the drug in a medical treatment.

\* \* \* \* \*